(12) United States Patent
Klettke et al.

(10) Patent No.: US 8,933,147 B2
(45) Date of Patent: Jan. 13, 2015

(54) ANTI-MICROBIAL DENTAL IMPRESSION MATERIAL

(75) Inventors: Thomas Klettke, Diessen (DE); Oliver Kappler, Weilheim (DE); Ingo R. Haeberlein, Weilheim (DE)

(73) Assignee: 3M Innovative Properties Company, St. Paul, MN (US)

( * ) Notice: Subject to any disclaimer, the term of this patent is extended or adjusted under 35 U.S.C. 154(b) by 864 days.

(21) Appl. No.: 12/093,869

(22) PCT Filed: Nov. 9, 2006

(86) PCT No.: PCT/US2006/043770
§ 371 (c)(1),
(2), (4) Date: May 15, 2008

(87) PCT Pub. No.: WO2007/061647
PCT Pub. Date: May 31, 2007

(65) Prior Publication Data
US 2009/0047620 A1   Feb. 19, 2009

(30) Foreign Application Priority Data
Nov. 17, 2005 (EP) .................................... 05025182

(51) Int. Cl.
A61K 6/10 (2006.01)
A61C 9/00 (2006.01)
A61L 2/16 (2006.01)

(52) U.S. Cl.
CPC .... A61L 2/16 (2013.01); A61K 6/10 (2013.01)
USPC ............................ 523/109; 433/214; 424/435

(58) Field of Classification Search
CPC ......... A61K 6/10; A61K 6/0067; A61K 6/08; A61K 6/093
USPC ......... 523/109, 113, 114, 115, 116, 118, 120; 433/214; 424/435
See application file for complete search history.

(56) References Cited

U.S. PATENT DOCUMENTS

| | | |
|---|---|---|
| 3,119,750 A | 1/1964 | Faucett |
| 3,427,345 A | 2/1969 | Holmen |
| 4,096,241 A | 6/1978 | Geistlich |
| 4,209,434 A | 6/1980 | Wilson |
| 4,298,738 A | 11/1981 | Lechtken |
| 4,324,744 A | 4/1982 | Lechtken |
| 4,356,296 A | 10/1982 | Griffith |
| 4,363,624 A | 12/1982 | Johnston |
| 4,385,109 A | 5/1983 | Lechtken |
| 4,500,339 A | 2/1985 | Young et al. |
| 4,503,169 A | 3/1985 | Randklev |
| 4,642,126 A | 2/1987 | Zador |
| 4,652,274 A | 3/1987 | Boettcher |
| 4,665,217 A | 5/1987 | Reiners |
| 4,695,251 A | 9/1987 | Randklev |
| 4,710,523 A | 12/1987 | Lechtken |
| 4,737,593 A | 4/1988 | Ellrich |
| 4,752,338 A | 6/1988 | Reiners |
| 4,836,853 A | 6/1989 | Gribi |
| 4,872,936 A | 10/1989 | Engelbrecht |
| 4,882,149 A | 11/1989 | Spector |
| 4,920,188 A | 4/1990 | Sakashita |
| 4,957,872 A | 9/1990 | Koever |
| 4,959,220 A | 9/1990 | Yamamoto et al. |
| 5,063,257 A | 11/1991 | Akahane |
| 5,076,844 A | 12/1991 | Fock |
| 5,130,347 A | 7/1992 | Mitra |
| 5,154,762 A | 10/1992 | Mitra |
| 5,176,899 A | 1/1993 | Montgomery |
| 5,210,083 A | 5/1993 | Pfirrmann |
| 5,227,413 A | 7/1993 | Mitra |
| 5,336,494 A | 8/1994 | Pellico |
| 5,367,002 A | 11/1994 | Huang |
| 5,393,516 A | 2/1995 | Rheinberger |
| 5,417,750 A | 5/1995 | Cohen et al. |
| 5,453,284 A | 9/1995 | Pellico |
| 5,501,727 A | 3/1996 | Wang |
| 5,520,725 A | 5/1996 | Kato |
| 5,545,676 A | 8/1996 | Palazzotto |
| 5,603,921 A | 2/1997 | Bowen |
| 5,679,779 A | 10/1997 | Heilmann |
| 5,760,152 A | 6/1998 | Heilmann |
| 5,762,502 A | 6/1998 | Bahn |
| 5,856,373 A | 1/1999 | Kaisaki |
| 5,859,089 A | 1/1999 | Qian |
| 5,871,360 A | 2/1999 | Kato |
| 5,889,183 A | 3/1999 | Herdeis |

(Continued)

FOREIGN PATENT DOCUMENTS

| | | |
|---|---|---|
| CA | 2247986 | 9/1997 |
| DE | 2628265 | 1/1977 |

(Continued)

OTHER PUBLICATIONS

Al-Omari et al., "A Microbiological Investigation Following the Disinfection of Alginate and Addition Cured Silicone Rubber Impression Materials", Eur. Journal Prosthodont. Rest. Dent., vol. 6, No. 3, 1998, pp. 97-101.

(Continued)

*Primary Examiner* — Michael Pepitone
(74) *Attorney, Agent, or Firm* — Nicole J. Einerson

(57) ABSTRACT

The invention relates to plastics which are self-disinfecting. The invention relates in particular to polyether or silicone based dental plastics and impression materials in which a biocidal material is incorporated. The dental impression material acc. to the invention comprises at least a polymerizable base paste BP and a non-aqueous catalyst paste CP, wherein the base paste BP comprises about 0.001 to about 10% by weight of a water-stable anti-microbial agent. Preferred anti-microbial agents are selected from the group consisting of Hexitidin, Cetypyridininumcloride (CPC), Chlorhexidine and its derivates (CHX) and Triclosan.

17 Claims, No Drawings

(56) References Cited

U.S. PATENT DOCUMENTS

| | | |
|---|---|---|
| 5,925,715 A | 7/1999 | Mitra |
| 5,962,550 A | 10/1999 | Akahane |
| 5,965,632 A | 10/1999 | Orlowski |
| 5,997,301 A | 12/1999 | Linden |
| 6,084,004 A | 7/2000 | Weinmann |
| 6,121,362 A * | 9/2000 | Wanek et al. .................. 524/448 |
| 6,187,833 B1 | 2/2001 | Oxman |
| 6,187,836 B1 | 2/2001 | Oxman |
| 6,251,963 B1 | 6/2001 | Köhler |
| 6,297,181 B1 | 10/2001 | Kunert |
| 6,306,206 B1 * | 10/2001 | Fischer et al. .................. 106/35 |
| 6,306,926 B1 | 10/2001 | Bretscher |
| 6,362,251 B1 | 3/2002 | Alkemper |
| 6,387,981 B1 | 5/2002 | Zhang |
| 6,435,873 B1 | 8/2002 | Burgio |
| 6,495,613 B1 | 12/2002 | Gangnus |
| 6,559,199 B1 | 5/2003 | Pusineri et al. |
| 6,566,413 B1 | 5/2003 | Weinmann |
| 6,572,989 B2 | 6/2003 | Bian |
| 6,624,236 B1 | 9/2003 | Bissinger |
| 6,696,058 B2 | 2/2004 | Pellico |
| 6,716,611 B2 | 4/2004 | Dana |
| 6,734,155 B1 | 5/2004 | Herbots |
| 6,752,989 B1 | 6/2004 | Haberlein |
| 6,765,036 B2 | 7/2004 | Dede |
| 6,765,038 B2 | 7/2004 | Mitra |
| 6,767,935 B1 | 7/2004 | Luchterhandt |
| 6,818,682 B2 | 11/2004 | Falsafi |
| 6,835,271 B1 | 12/2004 | Luchterhandt |
| 6,852,795 B2 | 2/2005 | Bissinger |
| 6,852,822 B1 | 2/2005 | Bissigner |
| 6,860,879 B2 | 3/2005 | Irion et al. |
| 6,894,144 B1 * | 5/2005 | Zech et al. .................. 528/394 |
| 6,960,079 B2 | 11/2005 | Brennan |
| 6,982,288 B2 | 1/2006 | Mitra |
| 7,147,471 B2 | 12/2006 | Frey |
| 7,173,074 B2 | 2/2007 | Mitra |
| 7,175,430 B1 | 2/2007 | Gasser |
| 7,435,558 B2 | 10/2008 | Haberlein et al. |
| 7,498,363 B2 * | 3/2009 | Bublewitz et al. ............ 523/109 |
| 2002/0150549 A1 | 10/2002 | Vogt et al. |
| 2003/0087986 A1 | 5/2003 | Mitra |
| 2003/0109596 A1 * | 6/2003 | Wanek et al. .................. 523/115 |
| 2003/0166737 A1 | 9/2003 | Dede |
| 2003/0166740 A1 | 9/2003 | Mitra |
| 2003/0195273 A1 | 10/2003 | Mitra |
| 2003/0198914 A1 | 10/2003 | Brennan |
| 2004/0029171 A1 | 2/2004 | Wagner |
| 2004/0081706 A1 | 4/2004 | Trainer et al. |
| 2004/0084812 A1 | 5/2004 | Grunwald et al. |
| 2004/0120901 A1 | 6/2004 | Wu |
| 2004/0122126 A1 * | 6/2004 | Wu et al. .................. 523/115 |
| 2005/0250871 A1 | 11/2005 | Bublewitz et al. |
| 2006/0069180 A1 * | 3/2006 | Bublewitz et al. ............ 523/109 |
| 2006/0159630 A1 | 7/2006 | Haeberlein |
| 2006/0177477 A1 | 8/2006 | Ash |
| 2007/0043141 A1 | 2/2007 | Wu |
| 2007/0173557 A1 | 7/2007 | Bublewitz et al. |
| 2007/0213460 A1 | 9/2007 | Ruppert et al. |
| 2008/0177217 A1 | 7/2008 | Polaschegg |

FOREIGN PATENT DOCUMENTS

| | | |
|---|---|---|
| DE | 4222821 | 1/1994 |
| DE | 19515976 | 10/1996 |
| DE | 19708782 | 3/1997 |
| DE | 19846556 | 4/2000 |
| DE | 198 49 388 | 5/2000 |
| DE | 19849388 | 5/2000 |
| DE | 19937091 | 2/2001 |
| DE | 19937092 | 2/2001 |
| DE | 19937093 | 2/2001 |
| DE | 102 61 241 | 7/2004 |
| EP | 0147021 A1 | 7/1985 |
| EP | 0 173 567 | 3/1986 |
| EP | 0 201 031 | 11/1986 |
| EP | 0 201 778 | 11/1986 |
| EP | 0 265 776 | 5/1988 |
| EP | 0300309 | 1/1989 |
| EP | 0 321 872 | 6/1989 |
| EP | 0 361 908 | 4/1990 |
| EP | 0 373 384 | 6/1990 |
| EP | 0 147 021 | 5/1991 |
| EP | 0 450 800 | 10/1991 |
| EP | 0 674 896 | 10/1995 |
| EP | 0674896 B1 | 10/1995 |
| EP | 0 824 019 | 2/1998 |
| EP | 1 334 710 | 8/2003 |
| EP | 0950669 | 9/2004 |
| FR | 2707660 | 1/1995 |
| GB | 976301 | 11/1964 |
| JP | 51-67346 | 6/1976 |
| JP | 62-201806 | 9/1987 |
| JP | 2007112910 | 5/1995 |
| JP | 407265097 | 10/1995 |
| JP | 40800267 | 1/1996 |
| JP | 9256226 | 9/1997 |
| JP | 2004331535 | 11/2004 |
| JP | 2004352617 | 12/2004 |
| KR | 2004005200 A | 1/2004 |
| WO | WO 88/02600 | 4/1988 |
| WO | WO 89/10736 | 11/1989 |
| WO | WO 90/06138 | 6/1990 |
| WO | WO 94/03174 | 2/1994 |
| WO | WO 96/29978 | 10/1996 |
| WO | WO 97/42825 | 11/1997 |
| WO | WO 98/48766 | 11/1998 |
| WO | WO 98/48766 | 11/1999 |
| WO | WO 00/38619 | 7/2000 |
| WO | WO 00/42092 | 7/2000 |
| WO | WO 01/07444 | 2/2001 |
| WO | WO 01/10389 | 2/2001 |
| WO | WO 01/30304 | 5/2001 |
| WO | WO 01/30305 | 5/2001 |
| WO | WO 01/30306 | 5/2001 |
| WO | WO 01/30307 | 5/2001 |
| WO | WO 01/37787 | 5/2001 |
| WO | WO 01/49241 | 7/2001 |
| WO | WO 01/64175 | 9/2001 |
| WO | WO 01/92271 | 12/2001 |
| WO | WO 02/06820 | 1/2002 |
| WO | WO 02/06820 | 6/2002 |
| WO | WO 02/068679 | 9/2002 |
| WO | WO 2004/058193 | 7/2004 |
| WO | WO 2004093876 A2 * | 11/2004 ......... A61K 31/4741 |
| WO | WO 2005/011377 | 2/2005 |
| WO | WO 2005/077321 | 8/2005 |

OTHER PUBLICATIONS

Bergman, "Disinfection of Prosthodontic Impression Materials: A Literature Review", The International Journal of Prosthodontics, vol. 2, No. 6, 1989, pp. 537-542.

Best et al., "Comparative Mycobactericidal Efficacy of Chemical Disinfectants in Suspension and Carrier Tests", Applied and Environmental Microbiology, vol. 54, No. 11, Nov. 1988, pp. 2856-2858.

Denton, "Chlorhexidine", Sterilants, Disinfectants, and Antiseptics, Chapter 15, 5$^{th}$ Edition, 2001, pp. 321-337.

Flanagan D.A. et al, "Antimicrobial Activities of Dental Impression Materials", Dental Materials, vol. 14, No. 6, Nov. 1998, pp. 399-404.

Fraud et al., "Effects of Ortho-Phthalaldehyde, Glutaraldehyde and Chlorhexidine Diacetate on *Mycobacterium chelonae* and *Mycobacterium abscessus* Strains with Modified Permeability", Journal of Antimicrobial Chemotherapy, vol. 51, 2003, pp. 575-584.

Lepe Xavier et al., "Wettability, Imbibition, and Mass Change of Disinfected Low-Viscosity Impression Materials", The Journal of Prosthetic Dentistry, vol. 88, No. 3, Sep. 2002, pp. 268-276.

Powell et al., "The Presence and Indentification of Organisms Transmitted to Dental Laboratories", The Journal of Prosthetic Dentistry, vol. 64, 1990, pp. 235-237.

(56) References Cited

OTHER PUBLICATIONS

Rios et al., "Effects of Chemical Disinfectant Solutions on the Stability and Accuracy of the Dental Impression Complex", The Journal of Prosthetic Dentistry, vol. 76, No. 4, 1996, pp. 356-362.
Samaranayake et al., "Carriage of Oral Flora on Irreversible Hydrocolloid and Elastomeric Impression Materials", The Journal of Prosthetic Dentistry, vol. 65, 1991, pp. 244-249.
Sofou et al., "Contamination Level of Alginate Impressions Arriving at a Dental Laboratory", Clin Oral Invest, vol. 6, 2002, pp. 161-165.
Utzinger et al., "AIDS in Dental Medicine", SWISS Dent, vol. 7, 1986, pp. 17-27.
Rhodes, C. et al., "Evaluation of an Alginate Substitute Using Specification Requirements", Journal of the American Dental Association, vol. 108, Feb. 1984, pp. 210-211.
Kondyukov et al. (Russian Journal of Organic Chemistry; vol. 43, No. 4/Apr. 2007; 635-636).
Gorman, et al., "A Comparative Study of the Microbial Anti-Adherence Capacities of Three Antimicrobial Agents," Journal of Clinical Pharmacy and Therapeutics, 1987, vol. 12, pp. 393-399, XP002909130.
Reynolds, et al., "Taurolin as an Oral Rinse I. Antimicrobial Effects In Vitro and In Vivo," Clinical Preventative Dentistry, Bd. 13, Nr. 2, 1991, pp. 13-22, XP009029748.
Bredereck et al., "Uber CH-aktive Polymerisationsinitiatoren XIII. Mitt. Polymerisationen and Polymerisationsinitiatoren," Die Makromolekulare Chemie, 1966, 92:70-90 (in German, Summary in English on p. 70).
"Cytochrome c—from Wikipedia, the free encyclopedia" datasheet [online]. Wikimedia Foundation, Inc., last modified on 14:03, Jan. 18, 2007 [retrieved on Jan. 19, 2007]. Retrieved from the Internet: <URL://http://en.wikipedia.org/wiki/Cytochrome c>; 2 pgs.
Derango et al., "Enzyme-mediated Polymerization of Acrylic Monomers," Biotechnology Techniques, Nov./Dec. 1992; 6(6):523-526.
Durand et al., "Enzyme-mediated Radical Initiation of Acrylamide Polymerization: Main Characteristics of Molecular Weight Control," Polymer, 2001; 42(13):5515-5521.
Emery et al., "Free-radical Polymerization of Acrylamide by Horseradish Peroxidase-mediated Initiation," Journal of Polymer Science., Part A: Polymer Chemistry, 1997; 35(15):3331-3333.
Enzyme Nomenclature: 1992, Recommendations of the Nomenclature Committee of the International Union of Biochemistry and Molecular Biology, Webb, E., ed. (Academic Press, Inc.: San Diego, CA) 1992; p. 112.
"Enzymatic Nomenclature Recommendations of the Nomenclature Committee of the International Union of Biochemistry and Molecular Biology on the Nomenclature and Classification of Enzyme-Catalyzed Reactions," [online]. Department of Chemistry, Queen Mary University of London. Last updated on Jun. 3, 2003 [retrieved on Jun. 19, 2003] [5 pgs]. Retrieved from the Internet: <URL:http://www.chem.qmw.ac.uk/iubmb/enzyme/>.
Iwahara et al., "Free-radical Polymerization of Acrylamide by Manganese Peroxidase Produced by the White-rot Basidiomycete Bjerkandera adusta," Biotechnology Letters, 2000; 22(17):1355-1361.
Iwahara et al., "Free-radical Polymerization of Acrylamide by Manganese Peroxidase Produced by the White-rot Basidiomycete Bjerkandera adusta," Wood Research, 2000; 87:21-22.
Iwata et al., "Initiation of Radical Polymerization by Glucose Oxidase Utilizing Dissolved Oxygen," Journal o/Polymer Science, Part A: Polymer Chemistry, 1991; 29(8):1217-1218.
Kalra et al., "Enzymatic Synthesis of Predominantly Syndiotactic Poly(Methyl Methacrylate)," Polymer Preprints (ACS, Div of Polymer Chemistry), 2000; 41(1):213-214.
Kalra et al., "Horseradish Peroxidase Mediated Free Radical Polymerization of Methyl Methacrylate," Biomacromolecules, 2000; 1(3):501-505.
Kalra et al., "In vitro Enzyme Catalyzed Polymerization," Abstract Pap—AM Chem. Soc., $220_{th}$ Poly—446 (2000) (1 page).
Lalot et al., "A Kinetic Approach to Acrylamide Radical Polymerization by Horse Radish Peroxidase-mediated Initiation," Polymer International, 1999; 48(4):288-292.
Mathis et al., "Properties of a New Glass Ionomer/Composite Resin Hybrid Restorative," Abstract No. 51, Journal o/Dental Research, 1987; 66:113.
Paquette et al., "A Convergent Three-component Total Synthesis of the Powerful Immunosuppressant (-)-Sanglifehrin A," Journal o/the Americal Chemical Society, vol. 124, Title page, Publication page and pp. 4257-4270 (16 pp. total) (2002).
Product Information Brochure, "Lifenza Bio Active Enzymes Enrich Your Life," Lifenza Co., Ltd, Seoul, Korea, (8 pgs total) (no date indicated).
Product Information Brochure, "Novora Anchor Enzyme Complex: Novora's Novel Platform Technology," Novora, Westlake Village, CA, 4 pgs (no date indicated).
Reynolds et al., "Taurolin As an Oral Rinse II. Effects on In Vitro and In Vivo Plaque Regrowth," Clinical Preventive Dentistry, Mar./Apr. 1991; 13(2):18-22.
Riggs et al., Chlorhexidine release from room temperature polymerizing methacrylate systems, Biomaterials, 2000; 21:345-351.
Sato et al., "Oxidation of 1,2,4,5-Tetramethoxybenzene to a Cation Radical by Cytochrome P450," Journal o/the American Chemical Society, vol. 122, Title page, Publication page and pp. 8099-8100 (4 pp. total) (2000).
Singh et al., "Enzyme-mediated Free Radical Polymerization of Styrene," Biomacromolecules, 2000; 1 (4):592-596.
Tae-kyung, "Lifenza to Present Enzyme for Mouth Care," The Korea Herald, p. 13, 1 pg (Oct. 10, 2000).
Taira et al., "A Study on Cytochrome c Oxidoreductase for Bonding a Tri-nbutylborane-Initiated Luting Agent to Dentin," Journal o/Biomedical Materials Research, 1999; 48(5):697-699.
Teixeira et al., "‴-Diketones as Key Compounds in Free-Radical Polymerization by Enzymes-Mediated Initiation," Macromolecules, 1999; 32(1):70-72.
Tischer et al., "Immobilized Enzymes: Methods and Applications," Topics in Current Chemistry, vol. 200, Springer Verlag, Berlin, Heidelberg, pp. 95-126 (1999).

* cited by examiner

ANTI-MICROBIAL DENTAL IMPRESSION MATERIAL

CROSS REFERENCE TO RELATED APPLICATIONS

This application is a national stage filing under 35 U.S.C. 371 of PCT/US2006/043770, filed Nov. 9, 2006, which claims priority to European Patent Application No. 05025182.6, filed Nov. 17, 2005, the disclosure of which is incorporated by reference in its/their entirety herein.

The present invention relates to anti-microbial dental impression materials with self disinfecting properties.

The invention relates to plastics which are self-disinfecting. The invention relates in particular to polyether or silicone based dental plastics and impression materials in which a biocidal material is incorporated.

Disinfection is a permanent requirement in dental practices and dental engineering laboratories. The transmission of germs from contaminated gloves or even bare hands via equipment, tools or materials to humans presents a risk for the patient, the dentist or dental technician and their assistants. Particularly in daily procedures in practice, the patient can come into contact with contaminated items or objects, allowing microorganisms to enter the blood stream through open wounds. During a session, as a result for example of using contaminated gloves when mixing an impression material and using contaminated optical conductors for the light polymerisation of radiation-curable filling materials, the risk of infection can be increased. Although the hygiene regulations are very strict, no absolutely reliable protection against infection can be guaranteed.

The primary function of dental impressions is to make replicas. However, during replica taking dental impressions come in contact with the oral environment and get contaminated with oral micro-organisms such as bacteria, yeasts and viruses [Sofou et al. (2002) Clin Oral Invest 6:161-165, Al-Omari et al. (1998) Eur J Prosthodont Rest Dent Vol 6:97-101, Samaranayake et al. (1991) J Prosthet Dent 65:244-249, Powell et al. (1990) J Prosthet Dent 64:235-237].

While mandatory for the patients health, disinfection of dental material before or after contact with the patient is also a tedious procedure, resulting in the waste of human resources in a dentist's practice. Generally, a disinfection step is performed before and after every contact of a dental material with a site to be treated in the patients mouth, which results in a considerable amount of time being wasted for a repetitive process.

Decontamination of dental impressions often starts by rinsing the impressions under running water. Afterwards, impression are generally chemically disinfected. Unfortunately, the replica accuracy is often comprised by exposure to chemical disinfectants for an extended period of time [Bergman (1989) Int J Prosthodont 2:537-542, Utzinger (1986) Swiss Dent 7:17-27, Rhodes et al. ADA, Chicago Ill.]. This can be problematic when taking precision impressions.

Therefore, it has been tried to provide an impression material which does not need to be chemically disinfected. Flanagan et al (1998, Dent Mater 14:399-404) describes anti-microbial alginate impression material with either quaternary ammonium compounds or chlorhexidine as anti-microbial systems which show an anti-microbial effect against bacteria and yeast. However, this approach is generally restricted to water-based systems. Furthermore these system are often not suitable for taking precision impressions.

It would also be advantageous to incorporate anti-microbial substances into non-aqueous based impression materials. In contrast to water-based impression materials that have to be poured immediately after impression taking, non-aqueous can be stored for an extended period of time which is beneficial.

A further problem which might arise from the use of anti-microbial agents in multi component impression materials is generally the fact that the anti-microbial agent is stored together with a reactive substance which often shows a tendency to polymerize upon storage. It is thus important that a anti-microbial agent does not detrimentally influence the storage stability of a multi component impression material more than avoidable.

In impression taking it is sometimes important that the dentist has sufficient time for syringing the prepared tooth or the prepared teeth as well as for tray filling. In this period of time the impression material remains viscous. Since dentists do not change impression materials very often it would be advantageous if multi component impression materials containing anti-microbial agents do not alter the working time in a significant manner.

U.S. Pat. No. 6,495,613 describes an approach to reduce adhesion of micro-organisms to plastics. Described are dental plastics and impression materials in which a biocidal material is incorporated and the adhesiveness of whose surface vis-a-vis microorganisms is reduced. No mention is made, however, of amounts of anti-microbial agents. The document is also silent with regard to the problem of setting times amended by the addition of anti-microbial agents and with regard to storage stability.

U.S. Pat. No. 5,733,949 describes an anti-microbial adhesive composition for dental use comprising the following polymerizable monomers: an anti-microbial monomer, a monomer containing at least one acidic group, and a monomer containing at least one alcoholic hydroxyl group, in combination with water and a polymerization catalyst.

EP 1 563 823 A2 describes a dental material based on alkoxysilane functional polyethers with a catalyst. While the general use of anti-microbial agents is mentioned, no instruction as to amounts and influence of the anti-microbial agents on the polymerization process and setting times are given.

It is thus desirable to have a water-free impression material suitable for taking precision impressions that can be de-contaminated simply by a brief rinse under running water, which has curing properties comparable to a material without self disinfecting properties and which can be stored over longer periods of time without losing its curability.

Furthermore it would be desirable to have an impression material that contains anti-microbial substances in order to prevent transfer of micro-organisms from the dental practitioner to the patient or vice versa. Also this material would be suitable to prevent transfer of microorganisms from the patients oral cavity to the blood stream during dental procedures. Taken together this material would be highly advantageous to improve hygienicity in the dental office and the dental lab with respect to impression taking.

SUMMARY OF THE INVENTION

A first aspect of the invention relates to a dental impression material comprising at least a polymerizable base paste BP and a non-aqueous catalyst paste CP, wherein the base paste BP comprises about 0.001 to about 10% by weight of a water-stable anti-microbial agent and the catalyst component comprises a catalyst for polymerizing the base component and wherein the anti-microbial agent does not increase the time measured until the start of polymerization after combining components BP and CP by more than a factor of about 2.

Such compositions enable the dental professional to simply rinse the impression material briefly under running water to ensure de-contamination of the material. This eliminates the need for a disinfection step in the dental practice, thereby saving time and reducing the uncertainty of the dental lab where information about a previous disinfection is often lacking. Also, it provides the dentist and lab with an anti-microbial impression that does not have to be poured out immediately and can be stored for extended periods of time.

Additionally such anti-microbial impressions have the advantage that they can be delivered essentially with little or no microbial contamination to the oral cavity of the patient thereby minimizing the risk that harmful microorganisms are delivered to the patient in the dental office. Impressions are often taken during operatory procedures that generate wounds in the oral cavity. An anti-microbial impression material therefore might prevent infection of the patients blood with microorganisms residing in the oral cavity or being delivered to the patient by dental staff.

In a further aspect of the invention, in the dental impression material the base paste BP comprises at least one compound comprising a polyether moiety or at least one compound comprising a siloxane moiety or both or at least one compound comprising a polyether moiety and a siloxane moiety.

It might be advantageous if in a dental impression material according to the invention, the base paste BP comprises at least one polyaddition product or at least one polycondensation product having an average of at least 2 aziridino groups or more and a molecular weight of at least about 500 or at least one organopolysiloxane A1 with at least two ethylenically unsaturated groups per molecule.

It can also be advantageous if a dental impression material according to the invention comprises
(A) at least one organopolysiloxane A1 with at least two ethylenically unsaturated groups per molecule in the base or in the catalyst paste or on both,
(B) organohydrogenpolysiloxanes with at least 3 SiH groups per molecule in the base paste,
(C) optionally organopolysiloxanes without reactive groups in the base paste or on the catalyst paste or in both,
(D) a catalyst for promoting the reaction between A and B in the catalyst paste,
(E) optionally hydrophilizing agents in the base paste or on the catalyst paste or in both,
(F) fillers in the base paste or on the catalyst paste or in both,
(G) optionally conventional dental additives, adjuvants, plasticizers and colorants in the base paste or in the catalyst paste or in both,
(H) optionally at least one silane with at least two alkenyl groups per molecule and/or a polyether containing at least one unsaturated hydrocarbon in one molecule.

The invention provides compositions of impression materials with biocidal and/or anti-microbial properties. Anti-microbials within the embodiment of the invention may be all anti-microbial compounds compatible with non-aqueous elastomeric dental material which include, among others, amino group containing organic anti-microbial agents, halogen containing organic antimicrobial agents, cationic surfactants, mono- and polyhydric phenols, anti-microbial peptides, bactericins, antibiotics, aldehydes p-hydroxy benzoates or parabenes, lauricidin, enzymes, proteins, fluoride, EDTA or natural oils with anti-microbial properties.

The invention further relates to a kit for producing dental materials, the kit comprising at least one composition according to the invention with at least a polymerizable base paste BP and a non-aqueous catalyst paste CP, the components BP and CP being present separated from one another and to containers and mixing devices containing a dental material according to the invention.

The invention also provides for the use of a dental impression material for taking impressions from the oral cavity of an animal or a human being as well as a method for the preparation of a dental impression material wherein a base paste BP is prepared by mixing about 0.001 to about 10% by weight of an anti-microbial agent with a polymerizable compound and a catalyst paste CP is prepared by mixing a catalyst for polymerizing the base component with at least one auxiliary compound and wherein the anti-microbial agent does not increase the time measured until the start of polymerization after combining components BP and CP by more than a factor of about 2 are disclosed.

Another aspect of the invention is a method for taking an impression from the oral cavity of an animal or a human being characterized in that the base paste BP and the non-aqueous catalyst paste CP of a dental impression material according to the invention are mixed to form a curable mixture and the curable mixture is placed in the oral cavity at the site where the impression is to be taken from and the curable mixture is left in place until it is sufficiently cured to be removed from the oral cavity essentially without disturbing the formed impression.

According to the invention, water is not a component needed for producing an impression with the inventive impression material.

The term "non-aqueous" within the meaning of the invention is to be understood as of not using water as an essential component for the catalyst paste to be mixed with the base paste to build an elastomer after curing. Thus, the catalyst paste and preferably also the base paste are substantially water-free. However, the non-aqueous paste(s) may contain unavoidable traces of water due to water traces that some components of the composition may contain like fillers or softeners or because of crystal water of components used in minor amount. These traces may add up to an amount of less than about 1% by weight or less than about 0.5% by weight or less than about 0.4% by weight or less than about 0.1% by weight or even less than 0.05% by weight with respect to the whole composition of the respective paste.

An anti-microbial agent is classified as "water-stable" within the meaning of the invention, if the anti-microbial agent does not degrade or decompose when dissolved in water or brought in contact with water producing other active anti-microbial agents, especially low molecular reaction products like active oxygene or chlorine. The dissolution of a salt in water producing ions or setting free crystal water is not considered as water-instable.

Currently used non-aqueous impression materials on the market are for instance VPS impression materials that employ a hydrosilylation curing mechanism and polyether impression materials that employ a ring-opening polymerization of aziridines as the curing mechanism.

DETAILED DESCRIPTION OF THE INVENTION

The invention features dental impression materials that have self-disinfecting properties. Generally, such materials do not have to be disinfected after contact with microorganisms, e.g., after handling the impression material before or after taking the impression or after removing the impression material from a patients mouth. The materials described according to the invention often only have to be rinsed with water in order to obtain a material which basically free of microbes. It is especially most advantageous for the person handling the impression materials that no disinfection is necessary before introducing the impression material into a patients mouth or after removing it from a patients mouth, rinsing with water is sufficient. The patient can also benefit from the material according to the invention since the impression material, which is often used at sites with open wounds, e.g., in the case of implants, is essentially free of microbes and thus the danger of infection is reduced.

It is expected that the material according to the invention can also benefit from an increased precision of the impressions taken with the material. Since usually no disinfection steps are necessary, the danger of alterations of the spatial representation of the site the impression was taken from is reduced.

Generally, all physiologically acceptable anti-microbial agents can be used according to the invention. However, the anti-microbial agent should, if possible, not alter the polymerization process more than avoidable, especially not more than acceptable with regard to the curing properties of the impression materials or with regard to the material properties of the cured impression material or with regard to the storage stability or with regard to two or more of these features.

Accordingly, in one embodiment of the invention the anti-microbial is selected from the group consisting of amino group containing organic anti-microbial agents, halogen containing organic anti-microbial agents, cationic surfactants, mono- and polyhydric phenols, anti-microbial peptides, bactericins, antibiotics, aldehydes p-hydroxy benzoates or parabenes, lauricidin, enzymes, proteins, fluoride, EDTA or natural oils with anti-microbial properties.

| Especially useful can be non-acidic compounds like | |
| --- | --- |
| Class | Compound |
| salts of phenolics or acids | salts of benzoic acid, salicylic acid, triclosan, thymol, phenol |
| Chlorhexidines (CHX) | chlorhexidine, chlorhexidine diacetate, chlorhexidine diacetate monohydrate, chlorhexidine dihydrobromide, chlorhexidine dihydrochloride, chlorhexidine dinitrate, chlorhexidine sulphate, chlorhexidine carbonate |
| qarternary ammonium compounds | benzalkonium chloride, substituted benzalkonium chlorides, cetylpyridinium chloride, N-(3-chloroallyl) hexaminium chloride, domiphene bromide, benzethonium chloride, methylbenzethonium chloride, didecyldimethylammonium chloride, octyldodecyldimethylammonium chloride |
| sugar alcohols | xylitol, sorbitol |
| Pyridinamines | hexetidine |
| Aldehydes | glutaraldehyde, phtaldehyde |

Furthermore, it can be advantageous to use combinations of anti-microbial compounds to generate an additive or synergistic effect. Especially preferred are combinations of chlorhexidine or derivatives thereof and aldehydes (glutaraldyde, phtaldehyde) and chlorhexidine or its derivatives and salts of phenolics or acids. It is also preferred to use acid adducts of chlorhexidine or its derivatives like e.g., acetates, chlorides, nitrates, sulfates or carbonates.

Chlorhexidine and its derivatives (hereinafter referred to as CHX) are commercially available in water-based solutions (e.g. a 20% aqueous solution of CHX digluconate, CAS 18472-51-0) or as a pure compound or as a salt. As additive to non-water based impression materials the pure compound (CAS 55-56-1) and CHX salts like CHX diacatate monohydrate (CAS 56-95-1) or CHX dihydrochloride (CAS 3697-42-5) are preferred.

Among the various combinations tested an addition of CHX to polyether materials can be especially effective. CHX also seems to be especially suited as an additive due in part to its well-known and proven anti-microbial action against Gram positive and Gram negative microorganisms including the oral *Streptococci* and *Lactobacilli*. CHX is bacteriostatic for *Mycobaterium*. CHX is also active against yeasts including *Candida albicans* and viruses including HIV, HBV, HCV, Influenza- and Herpes virus. A further advantage of CHX is its low toxicity.

Other anti-microbial compounds might be added to the impression materials, especially if it seems desirable to enhance the activity against certain classes of micro-organisms, e.g. Mycobacteria. Here, especially adding aldehyde- or phenyl-containing compounds can be advantageous. These compounds are known to be especially active against Mycobacteria.

The dental materials according to the invention are multi component materials which comprise at least a curable base paste BP and a catalyst paste comprising a catalyst for curing at least part of the material of the base paste. It has proven to be advantageous that the anti-microbial agent does not increase the time measured until the start of polymerization after combining components BP and CP by more than a factor of about 2. It is preferred if the time measured until the start of polymerization after combining components BP and CP is varied by the anti-microbial agent by a factor of between about 0.5 and about 1.7, especially between about 0.7 and about 1.3 or between about 0.8 and about 1.2.

It has further proven to be advantageous if the anti-microbial agent does not increase the time measured until the end of the polymerization reaction after combining components BP and CP by more than a factor of about 2. It is preferred if the time measured until the end of the polymerization reaction after combining components BP and CP is varied by the anti-microbial agent by a factor of between about 0.5 and about 1.7, especially between about 0.7 and about 1.3 or between about 0.8 and about 1.5.

At least a majority of the anti-microbial agent is generally present in the base paste BP. It can be advantageous if the catalyst paste CP is essentially free from anti-microbial agents. The amount of anti-microbial agent in the impression material according to the invention is about 0.001 to about 10% by weight. It can be advantageous if the amount of antimicrobial agent is in the range of about 0.05 to about 10% by weight or about 0.05 to about 6% by weight or about 0.05 to about 5% by weight. Preferably at least about 80% of this overall amount are present in the base paste BP. Most preferred this value is more than about 90%, e.g., about 95, about 99 or even about 100%.

According to the invention, the dental impression material can generally comprise any multiplicity of types of compounds which, when mixed shortly before taking an impression, result in the formation of a rubber like impression material due to a polymerization reaction. Generally, polyaddition, ring-opening polymerization and polycondensation are preferred types of polymerization reactions, polyaddition and ring-opening polymerization are most preferred.

Not necessarily comprised are alkoxyfunctionalized polyethers crosslinking via a condensation reaction as described in EP 1 563 823 A2.

The material according to the invention preferably comprises at least two components, BP and CP, wherein component BP is called a base paste and component CP is called a catalyst paste. The material according to the invention is typically a multi component material in the sense that the different components are combined in order to obtain a cured impression material, but are provided separately and are mixed shortly before application. A dental material according to the invention can comprise more than 2 components, e.g., 3 or 4, however, typically the number of components is 2, i.e., BP and CP.

While the art of preparing dental materials knows many different types of compounds, typically the curing mechanism is based either on polycondensation reactions of alkoxy slilyl groups which might take place in the presence of an acidic catalyst or salt of a strong acid and water or on polycondensation reactions of alkoxy slilyl groups with silanol groups in the presence of a catalyst without water or based upon the ring-opening polymerization e.g. of aziridines or based upon the polyaddition of silanes with olefinically unsaturated double bonds.

In one embodiment, polysiloxanes are used as part of the dental material according to the invention. The curing mechanism is a polyaddition reaction of silane moieties and olefinically unsaturated double bonds.

Thus, according to the invention, a curable material can, in addition to at least one anti-microbial agent, comprise:
(A) at least one organopolysiloxane A1 with at least two ethylenically unsaturated groups per molecule,
(B) organohydrogenpolysiloxanes with at least 3 SiH groups per molecule,
(C) optionally organopolysiloxanes without reactive groups,
(D) a catalyst for promoting the reaction between A and B
(E) optionally hydrophilizing agents,
(F) fillers,
(G) optionally conventional dental additives, adjuvants, plasticizers and colorants and
(H) optionally at least one silane with at least two alkenyl groups per molecule.

Component (A) according to the invention generally contains organopolysiloxanes with at least two pendant or terminal triorganosiloxy groups of which at least one of the three organic groups is a group with an ethylenically unsaturated double bond. Generally, the groups with an ethylenically unsaturated double bond can be located at any monomeric unit of the organopolysiloxane. It is, however, preferred, when the groups with an ethylenically unsaturated double bond are located on or at least near the terminal monomeric units of the polymer chain of the organopolysiloxane. In another preferred embodiment at least two of the groups with an ethylenically unsaturated double bond are located on the terminal monomeric units of the polymer chain.

The term "monomeric units" as used herein refers to repeating structural elements in the polymer that form the polymer backbone, unless expressly stated otherwise.

Preferred organopolysiloxanes of this general structure are represented by the following formula I:

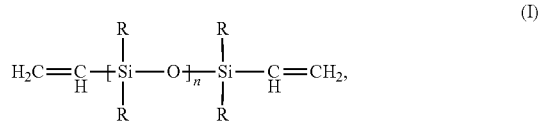

in which the radicals R independently from each other represent a non-substituted or substituted monovalent hydrocarbon group with 1 to 6 C atoms, which is preferably free from aliphatic multiple bonds and n is generally chosen such that the viscosity of the organopolysiloxanes lies between 4 and 100,000 mPas or between 6 and 50,000 mPas.

Generally, the radicals R can represent any non-substituted or substituted monovalent hydrocarbon group with 1 to 6 C atoms. Corresponding non-substituted or substituted monovalent hydrocarbon group with 1 to 6 C atoms can be linear or, if the number of carbon atoms exceeds 2, branched or cyclic. Generally, the radicals R can be equipped with all types substituents that do not interfere with at least one of the remaining constituents of the composition and do not interfere with the curing reaction. The term "interfere" as used herein refers to any influence of such a substituent on at least one of the remaining constituents of the composition or the curing reaction, or both, which is detrimental to the properties of the hardened product. The term "detrimental" as used herein refers to a change of properties of the precursors or the cured product that affect the usefulness of the precursors or the cured product related to the intended use of the precursors or the cured product in a negative manner.

In another preferred embodiment of the invention at least 50% of the radicals R represent methyl groups. Examples for other radicals R that can be present in the organopolysiloxanes according to formula I are ethyl, propyl, isopropyl, n-butyl, tert.butyl, the pentyl isomers, the hexyl isomers, vinyl, propenyl, isopropenyl, 2- and 3-n-butenyl, the pentenyl isomers, the hexenyl isomers, fluorine substitutes aliphatic radicals like 3,3,3-trifluoropropyl groups, cyclopentyl or cyclohexyl groups, cyclopentenyl or cyclohexenyl groups or aromatic or hereroaromatic groups like phenyl or substituted phenyl groups. Examples for such molecules are described in U.S. Pat. No. 4,035,453, the disclosure of which, especially the disclosure of the latter document regarding the above mentioned molecules, their chemical constitution and their preparation, is expressly regarded as being part of the disclosure of the present document and is included herein by reference.

The preparation of molecules of the above mentioned formula I is generally known to the skilled person. The preparation of corresponding molecules can be achieved, e.g., according to standard procedures which are portrayed e.g. in J. Burghardt, Chemie und Technologie der Polysiloxane in "Silikone, Chemie und Technologie", Vulkan Verlag, Essen, 1989, pages 23-37.

Linear polydimethylsiloxanes of the above structure with the specified viscosity ranges for which the end groups consist of dimethylvinylsiloxy units and the other radicals R in the chain consist of methyl groups are particularly preferred.

Component (A), as described above, according to the invention comprises at least one constituents A1. It is also within the context of the invention that Component (A) comprises two constituents A1 and A2 or even more than two different constituents, e.g., of 3, 4, 5, 6, 7, 8, 9 or 10 or more constituents which would the be labelled A3, A4, A5, A6, A7, A8, A9 and A10 up to An for the n$^{th}$ constituent of n constituents overall.

If two of the constituents constituting component (A) are present, they can differ in their viscosity, e.g., by a factor of at least 2. This means that in the material according to the invention, of the different types of organopolysiloxanes as constituents of component (A), at least (A1) and (A2) have a different viscosity and the value for the viscosity of (A2) is preferably at least twice as high as the value for the viscosity of (A1) for the same type of viscosity measurement.

The term "constituents" as used herein with regard to the constituents of component (A) relates to organopolysiloxanes differing at least in their average molecular weight, related to their polydispersity after preparation, to a measurable extent. The invention thus does not regard polymers of different chain lengths as obtained within a process for the preparation of one type of polymer within the achieved polydipersity of the chosen method as different constituents, under the proviso that the method of preparation results in a monomodal dispersion of polymer chain lengths.

It is another preferred embodiment of the invention when at least one constituent of (A) has a viscosity in the range of about 10 to about 1000 mPas, or about 50 to about 500 mPas or about 100 to about 300 mPas. In another preferred embodiment of the invention a constituent of (A) has a viscosity of about 500 to about 45000 mPas, e.g. from about 1000 to about 30000 mPas or about 3000 to about 15000 mPas, preferably a constituent of (A) has a viscosity of about 4000 to about 10000 mPas, e.g. from about 5000 to about 9000 mPas or about 6000 to about 8000 mPas.

A suitable method of measurement of the viscosity is performed with Haake Rotovisco RV20 (spindle MV, measuring cup NV). The viscosity is measured at 23° C. After activation and rectification of the system, spindle MV is installed. The material to be measured is then filled into the measuring cup NV. Without undue delay, the spindle is lowered into the measuring cup NV. The spindle should be covered by a layer of max. 1 mm. The material to be measured is tempered for 20 min at 23° C. The measurement is started by starting the machine and the viscosity values (mPas) are recorded starting 20 s after the start of measurement. Care should be taken to avoid any rotation or movement of the measuring cup NV. A value for the viscosity is obtained in mPas. The above mentioned method of measurement corresponds to DIN 53018-1.

Component (B) is preferably an organohydrogenpolysiloxane with at least 3 Si-bonded hydrogen atoms per molecule. This organohydrogenpolysiloxane preferably contains 0.01 to 1.7 wt.-% silicon-bonded hydrogens. The silicon valencies which are not saturated with hydrogen or oxygen atoms are saturated with monovalent hydrocarbon radicals R which, however, are free from ethylenically unsaturated bonds.

The hydrocarbon radicals correspond to the radicals R as defined above without the radicals having an ethylenically unsaturated bond. In a preferred embodiment of the invention, at least about 50%, preferably about 100% of the hydrocarbon radicals in component B which are bonded to silicon atoms are methyl radicals. Such components are also described in the literature mentioned above with regard to structure and preparation.

Suitable components (C) are organopolysiloxanes without reactive substituents as described e.g. in W. Noll "Chemie and Technologie der Silikone", Verlag Chemie Weinheim, 1968, pages 212 ff. These are preferably linear, branched or cyclic organopolysiloxanes where all silicon atoms are surrounded by oxygen atoms or monovalent hydrocarbon radicals with 1 to 18 carbon atoms which can be substituted or non-substituted. The hydrocarbon radicals can be methyl, ethyl, $C_2$-$C_{10}$ aliphatics, trifluoropropyl groups as well as aromatic $C_6$-$C_{12}$ radicals. Component (C) can contribute to thinning and expanding the rubber network and can act as a plasticizer for the cured material.

Polydimethylsiloxanes with trimethylsiloxy end groups are particularly preferred as component (C). Component (C) is used in the material according to the invention preferably in an amount of about 0 to about 40 wt.-%, preferably about 0 to about 20 wt.-% or about 0.1 to about 10 wt.-%.

Component (D) is preferably a platinum complex which can be prepared from hexachloroplatinum acid by reduction with tetramethyldivinyldisiloxane. Such compounds are known to the skilled person. Any other platinum compounds which catalyze or accelerate addition cross-linking of silanes with ethylenically unsaturated double bonds are also suitable.

Platinum-siloxane complexes as described, e.g. in U.S. Pat. No. 3,715,334, U.S. Pat. No. 3,775,352 and U.S. Pat. No. 3,814,730 are suitable, for example. The disclosure of these patents with regard to platinum complexes and their preparation is explicitly mentioned and expressly regarded as part of the disclosure of the present text.

The platinum catalyst is preferably used in quantities of about 0.00005 to about 0.05 wt.-%, particularly about 0.0002 to about 0.04 wt.-%, each calculated as elemental platinum and related to the overall weight of the material present with the components (A) to (H).

To control the reactivity of the addition reaction and to prevent premature curing, it may be advantageous to add an inhibitor which prevents the addition reaction for a specific period of time or slows the addition reaction down. Such inhibitors are known and described, e.g. in U.S. Pat. No. 3,933,880, the disclosure of which regarding such inhibitors and their preparation is expressly regarded as being part of the disclosure of the present invention. Examples of such inhibitors are acetylenic unsaturated alcohols such as 3-methyl-1-butyne-3-ol, 1-ethynylcyclohexane-1-ol, 3,5-dimethyl-1-hexyne-3-ol and 3-methyl-1-pentyne-3-ol. Examples of inhibitors based an vinyl siloxane are 1,1,3,3-tetramethyl-1,3-divinyl siloxane and poly-, oligo- and disiloxanes containing vinyl groups. The inhibitor is regarded as a part of component (D).

Component (E) is an agent generally capable of imparting a hydrophilic character to a composition or a hydrophilizing agent, which reduces the wetting angle of a drop of water or a water containing composition (e.g. a plaster suspension or the like) compared with the original silicon composition not containing component E, and thus promotes a better wettability of the overall composition in the damp mouth region and thus a better flow-on behaviour of the pastes.

A suitable measurement of the wetting angle to determine the hydrophilicity of impression materials is e.g. described in DE 43 06 997 A, page 5, the contents of this document with regard to this method of measurement being expressly mentioned by reference and being regarded as part of the disclosure of the present text.

The hydrophilizing agents are preferably not equipped with reactive groups so that they are not incorporated into the polysiloxane network. Suitable hydrophilizing agents are preferably wetting agents from the group of hydrophilic silicone oils which are not capable of being covalently incorporated into the hardened polymer network. Suitable hydrophilizing agents are described in WO 87/03001 and in EP 0 231 420 A1, the contents of which with regard to the hydrophilizing agents is expressly mentioned by reference and is regarded as part of the disclosure of the invention.

Furthermore, ethoxylated fatty alcohols which are e.g. described in EP 0 480 238 A1 are preferred. Furthermore, preferred hydrophilizing agents are polyether carbosilanes, e.g. known from WO 96/08230. Preferred are also the non-ionic perfluoralkylated surface-active substances described in WO 87/03001. Also preferred are the non-ionic surface-active substances which are described in EP-0 268 347 A1, i.e. the nonylphenolethoxylates, polyethylene glycol-mono- und diesters, sorbitan esters as well as polyethylene glycol-mono- and diethers listed therein. The contents of the latter documents with regard to hydrophilizing agents and their preparation is expressly mentioned by reference and is regarded as part of the disclosure of the invention.

The amounts of hydrophilizing agents used is about 0 to about 10 wt.-%, relative to the overall weight of all components, preferably about 0 to about 2 wt.-% and particularly preferably about 0.2 to about 1 wt.-%. The wetting angle of a drop of water on the surface of a cured material according to the invention measured after 3 minutes, is preferably less than about 60°, particularly preferably <about 50°, in particular <about 40°.

The compositions of the invention can also include a filler as component (F), preferably a mixture of hydrophobic fillers. A wide variety of inorganic, hydrophobic fillers may be employed such as silicas, aluminas, magnesias, titanias, inorganic salts, metallic oxides and glasses. It has been found to be possible to employ mixtures of silicone dioxides, including those derived from crystalline silicone dioxide, such as pulverized quartz (4-6 µm); amorphous silicone dioxides, such as a diatomaceous earth (4-7 µm); and silanated fumed silica, such as Cab-o-Sil TS-530 (160-240 m²/g), manufactured by Cabot Corporation.

The sizes and surface areas of the foregoing materials are controlled to control the viscosity and thixotropicity of the resulting compositions. Some or all of the foregoing hydrophobic fillers may be superficially treated with one or more silanating agents, as known to those of ordinary skill in the art. Such silanating may be accomplished through use of known halogenated silanes or silazides. Such fillers can be present in amounts of from about 5 to about 65 weight percent, especially about 10 to about 60 or about 20 to about 50 wt.-% of the composition.

Among the fillers which can be used according to component (F) are non-reinforcing fillers such as quarz, cristobalite, calcium silicate, diatomaceous earth, zirconium silicate, montmorillonite such as bentonite, zeolite, including molecular sieves such as sodium aluminium silicate, metal oxide powder such as aluminium or zinc oxide or their mixed oxides, barium sulphate, calcium carbonate, plaster, glass and plastic powder.

Suitable fillers are also reinforcing fillers such as e.g. pyrogenic or precipitated silicic acid and silica aluminium mixed oxides. The above mentioned fillers can be hydrophobized, for example by treatment with organosilanes or siloxanes or by the etherification of hydroxyl groups to alkoxy groups. One type of filler or also a mixture of at least two fillers can be used. The particle distribution is preferably chosen such that there are no fillers with particle sizes of more than about 50 µm.

The overall content of fillers (F) is in the range from about 10 to about 90%, preferably about 30 to about 80%, with regard to components (A) to (H).

A combination of reinforcing and non-reinforcing fillers is particularly preferred. In this respect, the quantity of reinforcing fillers ranges from about 1 to about 10 wt.-%, in particular from about 2 to about 5 wt.-%.

The difference in the named overall ranges, i.e. about 9 to about 70 wt.-%, in particular about 28 to about 55 wt.-% is accounted for by non-reinforcing fillers.

Pyrogenically-prepared highly-disperse silicic acids which have preferably been hydrophobized by surface treatment are preferred as reinforcing fillers. The surface treatment can be carried out, for example with dimethyldichlorosilane, hexamethyldisilazane, tetramethylcyclotetrasiloxane or polymethylsiloxane.

Particularly preferred non-reinforcing fillers are quartzes, cristobalites and sodium aluminium silicates which can be surface-treated. The surface treatment can generally be carried out with the same methods as described in the case of the strengthening fillers.

Furthermore, the dental materials according to the invention can optionally contain additives such as plasticizers like paraffin oil, pigments, anti-oxidizing agents, release agents and the like as component (G). For example, a chemical system may be employed to diminish the presence or degree of hydrogen outgassing which may be typically generated as a result of the vinyl polymerization. The composition thus may comprise a finely divided platinum metal that scavenges for and takes up such hydrogen. The Pt-metal may be deposited upon a substantially insoluble salt having a surface area of between about 0.1 and about 40 m²/g. Suitable salts are barium sulphate, barium carbonate and calcium carbonate of suitable particle sizes. Other substrates include diatomaceous earth, activated alumina, activated carbon and others. The inorganic salts are especially preferred to imply improved stability to the resulting materials incorporating them. Dispersed upon the salts is about 0.2 to about 2 parts per million of platinum metal, based upon the weight of the catalyst component. It has been found that employment of the platinum metal dispersed upon inorganic salt particles substantially eliminates or diminishes hydrogen outgassing during curing of dental silicones.

The materials according to the invention contain such additives in quantities of about 0 to about 2 wt.-%, preferably about 0 to about 1 wt.-%.

Component (H) according to the invention is optional and can contain at least one silane compound with at least 2 ethylenically unsaturated groups. Preferred silane compounds follow the general formula II

$$Si(R^1)_n(R^2)_{4-n} \quad (II)$$

wherein $R^1$ is a linear, branched or cyclic monovalent ethylenically unsaturated substituent which can undergo an addition reaction with SiH-groups, having from 2 to 12 carbon atoms, $R^2$ is a monovalent radical without groups that can undergo an addition reaction with SiH-groups or have a detrimental influence on such a reaction with 1 to 12 carbon atoms and n is 2, 3 or 4. Especially preferred radicals $R^1$ are vinyl, allyl and propargyl, especially preferred radicals $R^2$ are linear or branched $C_1$-$C_{12}$ alkyl groups.

Further preferred silane compound follow the general formula III:

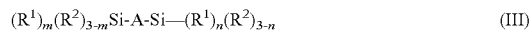

$$(R^1)_m(R^2)_{3-m}Si\text{-}A\text{-}Si\text{—}(R^1)_n(R^2)_{3-n} \quad (III)$$

wherein $R^1$ and $R^2$ and n are independently from each other defined as above, a is a bivalent linear or branched or alicyclic, heterocyclic, aromatic or heteroaromatic group with 1 to 10000 carbon atoms which can contain nitrogen or oxygen atoms and m is 2 or 3, preferably 3. Examples for bivalent radicals A are ethylene, propylene, butylene, penylene, hexylene, heptylene, octylene, nonylene, decylene, —$H_2C$—Ar—$CH_2$—, —$C_2H_4$—Ar—$C_2H_4$— with Ar being an aromatic bivalent radical, preferably phenyl, or bivalent polyether radicals of the general type —$CH_2CH_2CH_2$—O—$[C_aH_{2a}O]_b$—$CH_2CH_2CH_2$— with $1 \le a \le 5$ and $0 \le b \le 2000$.

Also suitable as component (H) can be silane dendrimers. Generally, three-dimensional, highly-ordered oligomer and polymer compounds are described as dendrimers, which are synthesized starting from small core molecules by a constantly repeating sequence of reactions. Monomer or polymer molecules with at least one reactive site are suitable as a core molecule. This is converted in a uni- or multi-level reaction with a reactant which accumulates at the reactive site of the core molecule and for its part has two new reactive sites. The conversion of core molecule and reactant yields the core cell (generation zero). By repeating the reaction, the reactive sites in the first reactant layer are converted with further reactants, again at least two new branching sites being introduced into the molecule each time (1$^{st}$ generation).

The progressive branching leads to a geometrical growth of the number of atoms for each generation. As the overall size can only grow linearly because of the number of possible covalent bonds specified by the reactants, the molecules become more tightly packed from generation to generation and they change their shape from starfish-shaped to spherical. Dendrimers of the zero and each further generation can be dendrimers used as component (H) according to the invention. Preferred are those of the first generation although those of much higher generations can be used.

Dendrimers of the first or higher generations are obtained as a core molecule by conversion of tri- or tetraalkenyl silanes (preferably allyl and vinyl) in a first step with hydrogenchloro-silanes. These products are converted in a further step with alkenyl-Grignard compounds.

Silane dendrimers, the preparation and use as varnishes of which are known from DE 196 03 242 A1 and DE 195 17 838 A1 as well as from EP 0 743 313. A1. Dendrimers listed there are also suitable for the purpose according to the invention. Polyfunctional alkenyl compounds are furthermore suitable as cores.

Particularly suitable are trimethylolpropanetriallylether, tetrallylpentaerythrite, Santolink XI-100 (Monsanto), tetraallyloxyethane, 1,3,5-benzoltricarbonic acid triallyl ester, 1,2,4-benzoltricarbonic acid triallylester, 1,2,4,5-benzoltetracarbonic acid tetrallylester, triallyl phosphate, triallyl citrate, triallyl isocyanurate, triallyloxytriazine, hexaallylinosite, as well as general compounds which possess at least two ethylenically unsaturated groups which can be optionally substituted, for example O-allyl, N-allyl, O-vinyl, N-vinyl or p-vinylphenolether groups.

Possible polyenes are also described in U.S. Pat. No. 3,661,744 and EP 0 188 880 A1. The polyene can have e.g. the following structure: (Y)—(X)m, m being an integer greater than or equal to 2, preferably 2, 3 or 4, and X being chosen from the —[RCR]$_f$, —CR=CRR, —O—CR=CR—R, —S—CR=CR—R, —NR—CR=CR—R group, f being an integer from 1 to 9 and the R radicals having the meanings H, F, Cl, furyl, thienyl, pyridyl, phenyl and substituted phenyl, benzyl and substituted benzyl, alkyl and substituted alkyl, alkoxy and substituted alkoxy as well as cycloalkyl and substituted cycloalkyl and each being able to be the same or different. (Y) is an at least difunctional organic radical which is constructed from atoms which are chosen from the C, O, N, Cl, Br, F, P, Si and H group.

The allyl- and/or vinyl esters of the at least difunctional carbonic acids are for example very suitable polyene compounds. Suitable carbonic acids for this are those with carbon chains of 2 to 20 C atoms, preferably 5 to 15 C atoms. Allyl or vinyl esters of aromatic dicarbonic acids such as phthalic acid or trimellithic acid are also very suitable. Allyl ethers of polyfunctional alcohols, preferably at least trifunctional alcohols are also suitable. Allyl ethers of trimethyl propane, pentaerythrite triallyl ether or 2,2-bis-oxyphenylpropane-bis-(diallyl phosphate) can be named as examples. Compounds of the cyanuric acid triallylester, triallyl triazintrione type and similar are also suitable.

Dendrimers of the above mentioned type and their preparation are described in U.S. Pat. No. 6,335,413 B1. The disclosure of this document with regard to such dendrimers and their preparation is expressly regarded as part of the disclosure of the invention.

Also suitable as component (H) can be polyethers containing at least one unsaturated hydrocarbon in one molecule, preferably having a number average molecular weight of about 200 to about 15000 as described e.g. in EP 1 290 998 B1.

The quantity ratios of components (A), (B) and (H) are preferably chosen such that about 0.5 to about 10 mol SiH units of component (B) are present per mol of unsaturated double bond of components (A) and (H). The amount of components (A), (H), and the (B) in the dental material is in the range of from about 5 to about 70 wt.-% relative to the total weight of all components. Preferably, the amount is in the range of from about 10 to about 60 wt.-% and particularly in a range of from about 15 to about 50 wt.-%.

The materials according to the invention can be prepared by mixing the components (A) to (H) and subsequently curing them in an addition reaction designated as hydrosilylizing in which, under the influence of the platinum catalyst (D), the SiH groups of the component (B) are added to the unsaturated groups of the components (A) and (H) respectively.

In a preferred embodiment the material according to the invention comprises:
about 5-70 wt.-% components (A)+(B)+(H),
about 0-40 wt.-% component (C),
about 0.00005-0.05 wt.-% component (D), calculated as elemental platinum and related to the overall weight of the material present with the compounds (A) to (H),
about 0-10 wt.-% component (E),
about 10-90 wt.-% component (F),
about 0-5 wt.-% component (G), and
about 0-50 wt.-% component (H).

In another preferred embodiment the material according to the invention comprises:
about 10-60 wt.-% components (A)+(B)+(H),
about 0-20 wt.-% component (C),
about 0.0002-0.04 wt.-% component (D), calculated as elemental platinum and related to the overall weight of the material present with the compounds (A) to (H),
about 0-2 wt-% component (E),
about 30-80 wt.-% component (F),
about 0-2 wt.-% component (G), and
about 0.1-20 wt.-% component (H).

For reasons of storage stability, the materials are preferably formulated in a two-component dosage form in which the overall component (B) is present in a so-called base paste BP. The overall component (D) is present physically separated from the base paste in a so-called catalyst paste CP. The components (A) or (H) or both can be either present in the catalyst or base paste, respectively, preferably a part of each of components (A) and (H) respectively being present in the base paste and a part of components (A) or (H) in the catalyst paste.

The volume ratios of catalyst and base pastes can be 10:1 to 1:10. Particularly preferred volume ratios of base paste:catalyst paste are about 1:1 and about 5:1 (5 parts base paste: 1 part catalyst paste). In the case of a volume ratio of 1:1, the components (A) to (H) can be distributed as follows as base and catalyst paste.

TABLE 1

| Component | Base paste (wt.-%) | Catalyst paste (wt.-%) | Total in base and catalyst paste (wt.-%) |
| --- | --- | --- | --- |
| (A) | 0-60 | 0-60 | 0-60 |
| (B) | 2-60 | — | 1-30 |
| (C) | 0-20 | 0-20 | 0-20 |
| (D) | — | 0.0001-0.1 | 0.00005-0.05 |
| (E) | 0-10 | 0-10 | 0-10 |
| (F) | 10-90 | 10-90 | 10-90 |
| (G) | 0-4 | 0-4 | 0-2 |
| (H) | 0-50 | 0-50 | 0-50 |

In the case of a volume ratio of 5 parts base paste to 1 part catalyst paste, preferred quantity ratios can be used as follows:

TABLE 2

| Component | Base paste (wt-%) | Catalyst paste (wt.-%) | Total in base and catalyst paste (wt.-%) |
|---|---|---|---|
| (A) | 0-60 | 0-60 | 0-60 |
| (B) | 1.2-36 | — | 1-30 |
| (C) | 0-24 | 0-20 | 0-20 |
| (D) | — | 0.00025-0.25 | 0.00005-0.05 |
| (E) | 0-10 | 0-10 | 0-10 |
| (F) | 10-90 | 5-90 | 10-90 |
| (G) | 0-2.4 | 0-4 | 0-2 |
| (H) | 0-10 | 0-10 | 0-10 |

With a volume ratio 5:1, both pastes can be filled into tubular film bags and later, shortly before use, can be mixed using a mixing and dosing device such as PENTAMIX™ (3M ESPE).

It can also be preferred according to the invention, if the curing of the dental material is effected by compounds with aziridino groups, e.g., in polyethers. Dental impression materials according to the invention comprising such aziridino compounds will also be called aziridino materials in the context of the present text.

In accordance with the invention the dental material can thus be a composition comprising at least a component Z, which is a polyaddition product or a polycondensation product having on average at least 2 aziridino groups or more and a molecular weight of at least about 500.

The term "molecular weight" refers to the number average of the molecular weight, as is conventionally determined for the individual classes of polymers by gel permeation chromatography (GPC) against a standard of defined molecular weight. Suitable measurement methods will be known to the person skilled in the art.

Furthermore, the determination of the molecular weights and the molecular weight distribution of polymeric polyols can be carried out, for example, by means of end group determination, for example by nuclear magnetic resonance (NMR) methods. Also suitable for the determination of the molecular weights and the molecular weight distribution of polymeric polyols is the determination of the hydroxyl value, as is described, for example, in Houben-Weyl "Methoden der organischen Chemie", 14/2, p. 17, Georg Thieme Verlag, Stuttgart, 1963. Also suitable is the procedure described in ASTM D2849—Method C.

A suitable method of determining the molecular weight ($M_w$ and $M_n$) and molecular weight distribution of organic diols can be carried out, for example, by means of GPC using a column combination PSS SDV 10,000 Å+Pss SDV 500 Å+Pss SDV 100 Å with column dimensions of 8×300 mm and a particle size of 5 μm. As a pre-column there is used a PSS SDV 100 Å having column dimensions of 8×50 mm and a particle size of 10 μm. THF stabilised with 200 ppm of Ionol, at a flow rate of 1.0 ml/min, is especially suitable as the mobile phase. As the detector there is used a refractive index (RI) detector; the injection volume for the samples (1% w/w weighed into the mobile phase) is 100 μl. As the standard solution there is used a polystyrene standard series (0.1% w/w weighed into the mobile phase). The evaluation is carried out according to the principle of relative GPC using an automatic evaluation module (TurboSEC Software) by means of comparison of the volumes of sample eluted with the volumes of the polystyrene standard series eluted. $M_n$, $M_w$ and polydispersity are evaluated.

In principle all polymers which can be prepared by polycondensation methods are suitable in the context of the invention as polycondensation products, provided that they meet the requirements of the composition with respect to their preferred use as dental aziridino materials. Suitable polycondensation products are, for example, polyesters, polyacetals or polysiloxanes.

Among the known, variously constituted, polyesters, those that are obtainable by polycondensation of dicarboxylic acids with diols or by polycondensation of oxycarboxylic acids and that have a substantially linear structure are especially suitable for preparation of the starting materials. The concomitant use of small amounts of tri- or tetra-functional alcohols or carboxylic acids during the polycondensation is possible and, in many cases, even advantageous for the mechanical properties of the compositions obtainable from the polyesters with respect to the use thereof as dental materials.

A large number of polyols can be used as polyols for the preparation of the above-mentioned polyesters. They are, for example, aliphatic alcohols having from 2 to 40H groups per molecule. The OH groups may be either primary or secondary. Suitable aliphatic alcohols include, for example, ethylene glycol, propylene glycol, 1,4-butanediol, 1,5-pentanediol, 1,6-hexanediol, 1,7-heptanediol, 1,8-octanediol and higher homologues or isomers thereof, as the skilled person will obtain by stepwise extension of the hydrocarbon chain in steps of one $CH_2$ group or by introducing branches into the carbon chain. Also suitable are higher-functional alcohols such as, for example, glycerol, trimethylolpropane, pentaerythritol and also oligomeric ethers of the mentioned substances either alone or from a mixture of two or more of the mentioned ethers together.

The reaction products of low-molecular-weight polyfunctional alcohols having at least two hydroxyl groups with allylene oxides, so-called polyethers, may also be used as polyols. The alkylene oxides preferably have from 2 to 4 carbon atoms. Suitable polyols are, for example, the reaction products of ethylene glycol, propylene glycol, butanediol or hexanediol isomers with one or more of the following alkylene oxides: ethylene oxide, propylene oxide or butylene oxides like tetrahydrofurane. Furthermore, the reaction products of polyfunctional alcohols such as glycerol, trimethylolethane or trimethylolpropane, pentaerythritol or sugar alcohols, or mixtures of two or more thereof, with the mentioned alkylene oxides, forming polyether polyols are also suitable.

Appropriate polyethers are brought about in a manner known to the person skilled in the art by reaction of the starting compound having a reactive hydrogen atom with alkylene oxides, for example ethylene oxide, propylene oxide, butylene oxide, styrene oxide, tetrahydrofurane or epichlorohydrine or mixtures of two or more thereof.

Suitable starting compounds are, for example, water, ethylene glycol, 1,2- or 1,3-propylene glycol, 1,4- or 1,3-butylene glycol, 1,6-hexanediol, 1,8-octanediol, neopentyl glycol, 1,4-hydroxymethylcyclohexane, 2-methyl-1,3-propanediol, glycerol, trimethylolpropane, 1,2,6-hexanetriol, 1,2,4-butanetriol, trimethylolethane, pentaerythritol, mannitol, sorbitol, or mixtures of two or more thereof.

For the preparation of appropriate polyesters there are suitable, for example, succinic acid, adipic acid, suberic acid, azelaic acid, sebacic acid, phthalic acid, isophthalic acid, terephthalic acid, trimellitic acid, phthalic anhydride, tetrahydrophthalic anhydride, hexahydrophthalic anhydride, tetrachlorophthalic anhydride, endomethylenetetrahydrophthalic anhydride, glutaric anhydride, maleic acid, maleic anhydride, fumaric acid, dimer fatty acid or trimer fatty acid or mixtures of two or more thereof. Where appropriate, minor amounts of monofunctional fatty acids may be present in the reaction mixture. Likewise suitable are unsaturated dicarboxylic acids such as maleic acid or fumaric acid and aromatic dicarboxylic acids, for example the phthalic acid isomers such as phthalic acid, isophthalic acid or terephthalic acid. As tricarboxylic acids there are suitable, for example, citric acid or trimellitic acid. The mentioned acids may be used singly or in the form of mixtures of two or more thereof.

The polyesters may, where appropriate, have a small proportion of carboxyl end groups. Polyesters obtainable from lactones, for example ε-caprolactone, or hydroxycarboxylic acids, for example ε-hydroxycaproic acid, may also be used.

Polyacetals are also suitable as polyol condensation products. Polyacetals are understood to be compounds such as are obtainable from glycols, for example diethylene glycol or hexanediol or a mixture thereof, with formaldehyde. Polyacetals which can be used in the context of the invention may also be obtained by the polymerisation of cyclic acetals.

As polysiloxanes there are suitable, in principle, all polysiloxanes which meet the requirements in terms of material properties with regard to the preferred use as dental materials. Special preference is given in the context of the invention, however, to, for example, the polysiloxane basic structures of the aziridino-group-carrying polysiloxanes described in DE 100 26 852 A1 from p. 2, line 55 to p. 8, line 20. The disclosure of the mentioned publication is regarded as part of the disclosure of the present text.

As polyaddition products there are suitable in the context of the invention, in principle, all polymers which can be prepared by polyaddition methods provided that they meet the requirements of the composition with regard to the preferred use thereof as dental materials. Suitable polyaddition products are, for example, polyurethanes or polyethers.

As polyurethanes there are suitable, in principle, all polymers which can be prepared by the reaction of polyols or polycarboxylic acids and isocyanates. Appropriate preparation methods will be known to the person skilled in the art; suitable polyols have already been described in the context of the present text as starting materials for the preparation of the above-mentioned polyesters.

In the context of a preferred embodiment of the invention, there are used, as constituents of the compositions according to the invention, polyaddition products, these preferably being polyethers.

As polyethers there are suitable, in principle, all polyether compounds which meet the requirements in terms of material properties with regard to the preferred use as dental materials. Suitable polyethers and processes for their preparation are described, for example, hereinbefore in the context of the present text. Especially suitable are polyether compounds as are obtainable by polyaddition of ethylene oxide, 1,2-propylene oxide, 1,2-butylene oxide or tetrahydrofuran or of mixtures of two or more of the mentioned compounds with the aid of a suitable starting compound and a suitable catalyst.

However, in the context of the invention, polyether compounds having a constituent of at least one repeating unit derived from 1,2-propylene glycol in the polyether chain are especially suitable. Accordingly, as basic polyether frameworks for the aziridino-group-carrying polymers contained in a composition according to the invention there are suitable, for example, polypropylene glycol, polyethylene glycol, polytetrafurane or copolymers thereof like ethylene glycol/propylene glycol copolymers or polytetrafurane/propylene glycol copolymers or polytetrafurane/ethylene glycol copolymers or mixtures of two or more thereof, especially polypropylene glycol or ethylene glycol/propylene glycol copolymers or polytetrafurane/ethylene glycol copolymers.

For example, polyether polyols which are prepared by copolymerisation of tetrahydrofuran and ethylene oxide in a molar ratio of from 10:1 to 1:1, preferably to 4:1, in the presence of strong acids, for example boron fluoride etherates, are suitable.

The polyether polyols which can be used for preparation of component Z have, on average, at least 2 hydroxyl groups but may also have up to 20 hydroxyl groups per molecule, for example on average up to about 3, 4, 5, 8, 10 or 15 hydroxyl groups.

The molecular weights ($M_n$) of the polyether polyols are usually in the range from about 600 to about 20,000 g/mol, preferably in the range from about 1,000 to about 10,000 g/mol.

The distribution of the structural units in the polymer which are based on different monomers can be organised randomly or in blocks.

Furthermore, suitable polyethers are described in DE 1 745 810, the disclosure of which in that respect is regarded as part of the disclosure of the present text.

The polymers contained, in the context of the invention, as component Z in the compositions according to the invention carry, on average, at least 2 aziridino groups.

The term "on average" is to be interpreted such in the context of the present text that a mixture of a large number of compounds of component Z may comprise both compounds having less than 2 aziridino groups and also compounds having more than 2 aziridino groups although, when seen over the entirety of the compounds of component Z, the average functionality of all molecules is, with respect to aziridino groups, 2 or more.

All mentioned types of polyaddition or polycondensation products can be provided with aziridino groups by means of any desired subsequent reactions known to the person skilled in the art. For example, it is possible first to introduce, into an appropriate polymer, substituents which are in turn capable of reacting with suitable aziridine derivatives. It is often possible to polymerise cyclic ethers, preferably epoxides, onto the chain so that products are obtained which at the end contain substituents which can react with aziridine. There come into consideration, for example, polyethers onto which halo-substituted epoxides, e.g. epibromohydrin, are polymerised. These substances contain short halo-substituted end groups, for example $CH_2Br$ groups when using epibromohydrin.

Suitable possible methods for providing the polymers with aziridino groups are mentioned, by way of example, in DE PS 1 745 810 or DE 100 26 852 A1; reference is expressly made to the mentioned publications, and the disclosure thereof with respect to functionalising polymers with aziridino groups is understood to be part of the disclosure of the present text.

Polymers suitable as component Z can carry the aziridino groups terminally or laterally, or terminally and laterally, but preferably terminally.

The aziridino polymers which can be used as component Z should preferably have a dynamic viscosity η of from 10 to about 500 Pa*s, especially from about 15 to about 300 Pa*s (23° C., measured with a rotary viscometer of the CVO 120 HR type from the company Bohlin Instruments GmbH Pforzheim at 23° C., plate-plate geometry, plate diameter: 20 mm, or plate-cone geometry, shear rate 20 $s^{-1}$).

A preferred viscosity range is from about 20 to about 180 Pa*s at 23° C.

The aziridino equivalent for the compounds used as component Z in the context of the invention is from about 250 to about 25,000 g/equivalent, especially from about 400 to about 10,000 g/equivalent.

A component (Z) which can be used in accordance with the invention may comprise only one type of aziridino polymer. It is, however, likewise possible for a component (Z) which can be used in accordance with the invention to comprise two or more different types of aziridino polymers, for example 3, 4 or 5 different types.

A "type of polymer" is understood, in the context of the present invention, to be a polymer as results from the polyaddition or polycondensation of selected monomers under the selected reaction conditions. A type of polymer can accordingly include polymer molecules of differing chemical constitution and differing molecular weight, depending on the reaction conditions selected. However, two reactions carried out using identical monomer compositions under identical reaction conditions always result, in accordance with the invention, in identical types of polymer. Two reactions which are carried out using identical monomers but under different reaction conditions may result in identical types of polymers but need not do so. The crucial factor therein is whether there are identifiable differences—in terms of chemical constitution, molecular weight and further parameters which can be determined—that are of relevance to the material properties. Two reactions which are carried out using different monomer compositions always result, in accordance with the invention, in different types of polymers.

In the context of a preferred embodiment, a component (Z) which can be used comprises one type or two different types of aziridino polymer, especially only one type.

A component (Z) according to the invention preferably comprises at least one aziridino polymer which has, as its basic framework, a polyether, preferably a polyether based on polytetrahydrofuran (poly-THF) or a propylene glycol/ethylene glycol copolymer or an ethylene glycol/tetrahydrofuran copolymer, irrespective of the manner of preparation.

Further polyaziridino compounds suitable for use in component (Z) are mentioned, for example, in the Offenlegungsschrift DE 15 44 837, p. 3-p. 14.

In addition to components (Z), an aziridino material according to the invention can also comprise an additive or a mixture of two or more additives.

Suitable additives are, for example, compounds that bring about plasticising of the cured dental material compositions. Such compounds can be both typical plasticisers as are also provided for other polymer systems and also esters of polycarboxylic acids, polyaromatic compounds and sulfonic acid esters or compounds which, besides the plasticising, also bring about other effects such as a surfactant action, an increase in structural strength and an improvement in flow behaviour.

Typical plasticisers are, for example, compounds of the ester type such as $C_{12}$- to $C_{15}$-alkyl lactates, ethyl or butyl esters of citric acid or of acetylcitric acid, phthalic acid esters of relatively long, branched alcohols such as bis(2-ethylhexyl)phthalate or phthalic acid polyester, $C_2$- to $C_{22}$-dialkyl esters of $C_2$- to $C_6$-dicarboxylic acids such as bis(2-ethylhexyl) adipate, dioctyl maleate, diisopropyl adipate, aromatic and aliphatic sulfonic acid esters such as $C_2$- to $C_{20}$-alkylsulfonic acid esters of phenol or of $C_1$- to $C_{22}$-alkanols or typical aromatic plasticisers such as polyphenyls in a wide viscosity range, including wax-like polyphenyls such as are obtainable, for example, from the Monsanto company, dibenzyltoluene, isomeric mixtures of $C_{20}$ to $C_{40}$ aromatic compounds, with preference being given to the use of mixtures of plasticisers of the ester type and aromatic type.

An example of a preferred plasticiser mixture is a mixture of acetyl tributyl citrate and dibenzyltoluene.

Likewise suitable as additives are triacyl esters of glycerol of non-animal origin. Suitable additives can consist of, for example, modified fats of vegetable origin such as hydrogenated palm oil or soybean oil or synthetic fats.

Suitable fats are described in DE 197 11 514 A1 (e.g. p. 2, line 65—p. 3, line 22), to the full content of which reference is here made. Avocado oil, cottonseed oil, groundnut oil, cocoa butter, pumpkin seed oil, linseed oil, maize germ oil, olive oil, palm oil, rice oil, rapeseed oils, safflower oil, sesame oil, soybean oil, sunflower oil, grapeseed oil, wheat germ oil, Borneo tallow, fulwa butter, hemp oil, illlipé butter, lupin oils, candlenut oil, kapok oil, katiau fat, kenaf seed oil, kekuna oil, poppy seed oil, mowrah butter, okra oil, perilla oil, sal butter, shea butter and tung oil are especially suitable, provided that the fats in question have been hydrogenated before use. Suitable hydrogenated fats are considered to be those whose iodine value is less than 20 (measured in accordance with the DGF [German Society for Fat Science] standard C-V 11 Z2). Fat hydrogenation procedures are described, for example, in "Ullmanns Enzyklopädie der industriellen Chemie", 4th edition, volume 11, p. 469.

Mixtures of those naturally occurring fats, and also synthetically prepared fats such as Softisan 154 or Dynasan 118 (from Hüls) can likewise be used. The preparation of such synthetic triacyl glycerides is relatively simple for the person skilled in the art and can be carried out by starting from glycerol and the appropriate fatty acid methyl esters. Such esterification reactions are described in, inter alia, "Houben-Weyl, Methoden der Organischen Chemie", Vol. E5/Part 1, p. 659 ff.

Preferred triacyl glycerides correspond to the formula:

in which $R^1$, $R^2$ and $R^3$ denote, each independently of the others, $C_{11}H_{23}CO$, $C_{13}H_{27}CO$, $C_{15}H_{31}CO$ or $C_{17}H_{35}CO$. Mixtures of such triacyl glycerides also come into consideration.

Likewise suitable as additives are liquid polymeric compounds having molecular weights of more than about 2000 g/mol, for example types of compounds such as polyethers, polyesters, polyurethanes, polycarbonates or polyolefins, with hydroxyl, ether, alkyl and acyl groups being suitable as end groups.

For example, dihydroxy or diacetyl polyethers comprising oxytetramethylene and oxydimethylene units in a ratio of from 4:1 to 3:1 and molecular weights in the range from about 3000 to about 8000 g/mol are suitable as additives.

Polypropylene oxide polyols and/or copolymerisation products and/or block copolymerisation products of ethylene oxide and propylene oxide having hydroxyl or acetyl end groups can also be used in admixture with the mentioned polyethers or on their own as additives.

In the case of block copolymerisation products having molecular weights greater than about 2000 g/mol, the solubility-promoting action of those surfactant-like compounds can be additionally utilised.

Furthermore, as a result of selecting and mixing the aforementioned polyether derivatives, the flow behaviour and the requisite adjustment of hydrophilicity and hydrophobicity of the mixed preparations can be decisively influenced.

The compositions according to the invention may also comprise, as additives, from about 10 to about 20% by weight fillers having reinforcing action, as mentioned above.

The preparations according to the invention may also comprise further additives such as dyes and coloured pigments, aromas or flavourings.

Acid capture agents, which fully neutralise acids, acid groups or acid-cleaving substances present in the starting materials, may also be used as additives. For example, amines, especially tertiary amines, are suitable for the purpose.

As additives there may also be used modifying agents as are described in DE 32 45 052 (p. 4-p. 6), with reference being made expressly to the modifying agents mentioned therein, which are understood as being part of the disclosure of the present text.

The above-mentioned additives are usually contained in a composition according to the invention in an amount of from about 0 to about 60% by weight, for example from about 10 to about 40% by weight.

The dental aziridino material according to the invention is present in at least one base paste BP and at least one catalyst paste CP. The base paste BP comprises at least one compound Z and the catalyst paste CP comprises at least one catalyst for the cross-linking of at least part of the base paste BP.

The catalyst paste CP comprises at least one initiator substance which triggers polymerisation of the aziridino-group-carrying constituents of base paste BP and, as a result, curing of the dental material as a whole.

As initiator substances there come into consideration, in principle, all compounds triggering the polymerisation of aziridines, provided that they bring about a suitable setting rate and suitable elastomeric properties for the cured dental material.

Accordingly, for use in two-component impression materials based on the polyether derivatives described hereinbefore there are suitable those initiator substances which make possible curing of the mixed preparation at room temperature in a period of from about 1 to about 20 minutes to form a resilient solid body, that solid body meeting the requirements for a resilient impression material according to DIN/EN 2482 and having a Shore A hardness (DIN 53 505) of at least 20 after 24 hours.

In the context of a preferred embodiment of the invention, a dental material is so adjusted with respect to components BP and CP that it has after mixing of the component BP and the catalyst paste CP at room temperature, within a period of about 20 minutes or less, a Shore A hardness of at least about 50% of the value of Shore A hardness reached after 24 hours.

As initiator substances in a catalyst paste CP which is suitable according to the invention there may be used, in principle, all known initiators. There are advantageously used those initiators or initiator systems which permit simple adjustment of the course of curing, which do not bring about subsidiary effects and which make it possible to achieve, reproducibly, the requisite level of mechanical properties.

A summarising description of the initiator substances used for the curing of N-alkylaziridino compounds is contained in, for example, O. C. DERMER, G. E. HAM, "Ethylenimine and other Aziridines" Academic Press (1969).

Trialkylsulfonium salts as are described in, for example, U.S. Pat. No. 4,167,618 (e.g.: column 2, line 36—column 4, line 32 and Examples) are especially suitable as initiator substances. The mentioned trialkylsulfonium salts are understood as being part of the disclosure of the present text.

In DE 914 325, the use of oxonium, ammonium and sulfonium salts as initiator substances is proposed (e.g.: p. 2, line 77—p. 3, line 100 and Examples), the initiator substances mentioned therein likewise being considered part of the disclosure of the present text.

In DE 100 18 918 A1, initiators are described which impart just a low degree of acidity to the catalyst component and which make possible a readily adjusted, relatively long processing time after mixing of the basic component and catalyst component has been carried out. Reference is expressly made also to the compounds mentioned therein and the initiator substances mentioned therein are likewise considered part of the disclosure of the present text.

The initiator compounds mentioned in U.S. Pat. No. 4,176,618 are especially suitable. The disclosure of that publication in respect of initiator substances is considered part of the disclosure of the present text.

In addition initiators mentioned in European patent application No. 05016531.5 are especially suitable. The disclosure of that publication in respect of initiator substances is considered part of the disclosure of the present text Initiator systems of that type are suitable for curing the basic components according to the invention at the requisite rate. By virtue of their use, the desired properties of the resilient solid body can be achieved.

DE 199 42 459 describes elastomeric materials having an improved catalyst component which are distinguished by increased extensibility. In accordance with that invention, boric acid complexes are used as initiators. Those initiators have likewise been found to be suitable for the curing of N-alkylaziridino polymers and can be used in the context of the present invention.

In the context of the invention, the following initiator compounds are preferably used: the zinc salt of p-toluenesulfonic acid, β-(S-lauryl-5-ethylsulfonium)butyronitrile tetrafluoroborate, dodecylbenzenesulfonic acid zinc salt, β-(S-lauryl-5-ethylsulfonium)-β-phenylacrylic acid butyl ester tetrafluoroborate.

A catalyst paste CP may also comprise, in addition to one of the above-mentioned initiator compounds or a mixture of two or more thereof, one or more additives. The additives already mentioned hereinbefore are suitable as additives.

The initiator compounds of component CP may be, for example, in the form of low-viscosity liquids or solids which may be difficult to incorporate uniformly in the more or less viscous masses of component B. In order to avoid that disadvantage, the initiator compounds may be brought into a viscous form corresponding to the particular intended application area, for example by incorporating fillers of large surface area, such as colloidal silica.

Also, the use of solutions of the initiator compounds in suitable plasticisers as component CP is often advantageous; by that means not only is it possible for extreme mixing ratios to be avoided but it is also possible for cross-linking agents that are solid at room temperature, e.g. acetyl tributyl citrate, to be conveniently incorporated into component CP.

The initiator compounds are generally contained in component CP in an amount of from 0.5 to 90% by weight, for example from 2 to 80% by weight or from about 5 to about 50% by weight.

The molar ratio of aziridino groups to anions of the initiator compounds is, in the context of the dental materials according to the invention, from about 3:1 to about 0.9:1, for example from about 2:1 to about 1:1, especially from about 1.8:1 to about 1.1:1.

The dental aziridino materials can be obtained, for example, from preparations containing, in total, about
- about 30 to about 80% by weight, preferably about 40 to about 71% by weight, aziridino-group-carrying compounds;

about 8 to about 40% by weight, preferably about 10 to about 25% by weight, compounds which bring about plasticising of the cured dental materials;

about 4 to about 25% by weight, preferably about 9 to about 20% by weight, fillers;

about 0.1 to about 60% by weight, preferably about 10 to about 40% by weight, further ingredients such as colorants, aromas, initiators, retarding agents, accelerators, rheological additives, consistency agents and surfactants.

Especially suitable components and formulations are described, for example, in the following patents and patent applications: DE 1745810, U.S. Pat. No. 3,453,242, U.S. Pat. No. 1,544,837, U.S. Pat. No. 4,167,618, DE 3245052, DE 3728216, EP 0421371, DE 4306997, DE 4321257, DE 19753461, DE 19740234, DE 10001747, DE 10018918.

The invention also relates to containers and mixing devices containing a dental material according to invention. Generally, as containers and mixing devices cartridges, sachets, impression trays, static and dynamic mixers and other mixing devices can be used.

The invention also relates to the use of a dental impression material for taking impressions from the oral cavity of an animal or a human being.

The invention further relates to a method for the preparation of a dental impression material wherein a base paste BP is prepared by mixing about 0.001 to about 10% by weight of an antimicrobial agent with a polymerizable compound and a catalyst paste CP is prepared by mixing a catalyst for polymerizing the base component with one or more auxiliary compounds and wherein the antimicrobial agent does not increase the time measured until the start of polymerization after combining components BP and CP by more than a factor of about 2.

The invention also relates to a method for taking an impression from the oral cavity of an animal or a human being characterized in that the base paste BP and the catalyst paste CP of a dental impression material according to the invention are mixed to form a curing mixture and the curing mixture is placed in the oral cavity at the site where the impression is to be taken from and the curing mixture is left in place until it is sufficiently cured to be removed from the oral cavity essentially without disturbing the formed impression.

The invention further relates to a method for disinfecting a dental impression material comprising the steps of providing a non-aqueous dental impression material as described in any of claims 1-10, which is set and germ contaminated and rinsing the set dental impression material with a non disinfecting liquid and leaving the impression material to dry or actively drying the impression material.

Generally, all types of non disinfecting liquids can be used for rinsing the dental impression material. In many cases water is preferred as non disinfecting liquid since it is usually present in those places where generally dental impression materials are handled, e.g. in dental offices or dental laboratories.

It can also be a preferred option to omit the step of using a disinfectant during the above described method for disinfecting, since the impression material according to the invention in most cases provides enough self-disinfecting activity to yield a basically sterile material after the above mentioned steps.

The invention also relates to a method of using a dental impression material as described in the invention for taking impressions from the oral cavity of an animal or a human being.

The invention also relates to a method for taking an impression from the oral cavity of an animal or a human, wherein the base paste BP and the catalyst paste CP of a dental impression material according to the invention are mixed to form a curing mixture and the curing mixture is placed in the oral cavity at the site where the impression is to be taken from and the curing mixture is left in place until it is sufficiently cured to be removed from the oral cavity essentially without disturbing the formed impression.

The invention is further explained by way of examples.

EXAMPLES

A laboratory system was worked out that models the clinical procedure of impression taking with concomitant contamination of the material, the removal of the material from the mouth and the subsequent cleaning by a brief rinse under tap water. The remaining contamination was determined by microbiological methods:

Impression material was applied into sterile Petri dishes. Filters loaded with *Streptococcus mutans* (DSM 20523) or stimulated human saliva were contacted with the material during setting. A *Strep. mutans* concentration of approx. 5E9 CFU/ml was chosen which is similar to the microorganismsl number found salviva. After setting, the material was removed from the contaminated filter and briefly rinsed with sterile water.

Remaining microorganisms were transferred to agar plates and the plates were incubated anaerobically at 37° C. to allow for growth of surviving microorganisms. Microorganisms growth was recorded as confluent growth, +++; many colonies, ++; few colonies, +; no growth, -.

If not otherwise indicated, % means % by weight.

Laboratory Test Method to Determine Setting Time

The start of setting was determined according to the following procedure: 0.5 g catalyst and 0.12 g base paste are mixed using a spatula without voids and bubbles within 45 seconds. Approximately half of the amount of the mixed paste is smoothed out on a mixing pad. The remaining amount is used to determine the start of setting. The paste remains stringy and flowable until a sharp transition point is reached, where the paste no longer flows and can no longer be shaped. The time from start of mix until this transition point is reached is defined as start of setting Results:

| Test material | Concentration of antimicrobial agent in the cured paste [%] | Time until start of polymerization [min] | Growth of *S. mutans* DSM 20523 |
|---|---|---|---|
| Impregum ™ Garant ™ L Duo Soft[1] | 0 | 2.6-2.8 | +++ |
| Impregum ™ Garant ™ L Duo Soft + hexetidine | 5.42 | 3.7 | - |
| Impregum ™ Garant ™ L Duo Soft + hexetidine | 4.04 | 2.3 | + |

| Test material | Concentration of antimicrobial agent in the cured paste [%] | Time until start of polymerization [min] | Growth of S. mutans DSM 20523 |
|---|---|---|---|
| Impregum ™ Garant ™ L Duo Soft + benzalkonium chloride | 1.14 | 4 | ++ |
| Express ™ Ultra-Light Body[2] | 0 | 1.6 | +++ |
| Express ™ Ultra-Light Body + chlorhexidine diacetate hydrate | 1 | 1.5 | – |
| Express ™ Ultra-Light Body + chlorhexidine diacetate hydrate | 5 | 1.6 | – |

[1]Aziridinopolyether based impression material
[2]Silicone based impression material Example Addition of CHX Diacetate Hydrate (CAS 56-95-1), to Impregum™ Garant™ L DuoSoft (Aziridinopolyether Based Impression Material)

| Chlorhexidine (%) as CHX diacetate hydrate (CAS 56-95-1) in cured paste | Growth of S. mutans (initial conc. 5E9 CFU/ml) | Growth of salivary microorganisms (initial conc. 5E7 CFU/ml) |
|---|---|---|
| 0 | +++ | +++ |
| <0.2 | +++ | n.d. |
| 0.4-0.5 | +/– | n.d. |
| 0.6-0.7 | – | n.d. |
| 0.8 | – | +/– |
| 1.5 | – | – |
| 3.6 | – | – |

Examples

Storage Stability

CHX was added to the following base paste (aziridinopolyether based impression material) using speed mixer:

58.0% with ethylene imine α,ω-difunctionalized polyether (polyether back bone is a copolymer EO/THF with a molecular weight of 6000)
13.6% fat (triscacylic ester of glycerine)
11.6% dibenzyl toluene
0.88% surfactant copolymer EO/PO
0.65% lauryl imidazole
13.9% diatomaceous earth
1.37% dyes, pigments, flavorings The resulting base pastes were reacted with the following catalyst paste:
19.3% sulfonium salt tetafluoroborate
40.5% acetyl tributyl citrate
3.5% surfactant copolymer EO/PO
12.1% diatomaceous earth
24.1% highly dispersed silica, surface treated
0.5% dyes, pigments, flavorings Gel points were determined as follows: 0.5 g of the respective base paste was mixed together with 0.12 g of Impregum™ Penta™ catalyst paste. Setting was determined using common oscillating rheometer (plate-plate geometry, 9 mm diameter) measuring G' and G". The gel point was determined (G'=G"). Measurement parameters are: 23° C., slot 1000 μm, frequency 1.0 Hz, deformation 0.01. The measurement started 30 seconds after catalyst and base paste were mixed for 30 seconds using a spatula.

The viscosity of the base paste was determined using the same geometry.

| Entry | CHX added to the base paste as | CHX (CAS 55-56-1) (%) in the cured paste | Gel point (G' = G") determined after storage [min:sec] 24 hrs (23° C.) | 6 months (36° C.) | Viscosity of the base paste at shear rates of 95/50/20 Pas determined after storage [Pa] 24 hrs (23° C.) | 6 months (36° C.) |
|---|---|---|---|---|---|---|
| 1 | — | — | 3:26 | 3:12 | 100/78/66 | 145/95/71 |
| 2 | CHX diacetate hydrate, CAS 56-95-1 | 0.1 | 3:38 | n.d. | n.d. | n.d. |
| 3 | CHX diacetate hydrate, CAS 56-95-1 | 0.3 | 3:34 | n.d. | n.d. | n.d. |
| 4 | CHX diacetate hydrate, CAS 56-95-1 | 0.5 | 3:28 | 3:09 | 96/72/58 | 133/90/69 |
| 5 | CHX diacetate hydrate, CAS 56-95-1 | 1.0 | 3:28 | n.d. | 103//75/61 | 136/92/69 |
| 6 | CHX diacetate hydrate, CAS 56-95-1 | 2.0 | 3:24 | 3:10 | 103/76/62 | 137/93/71 |
| 7 | CHX, CAS 55-56-1 | 2.0 | 3:25 | n.d. | n.d. | n.d. |
| 8 | CHX digluconate 20% in water, CAS 18472-51-0 | 2.0* | 12:24 | n.d. | n.d. | n.d. |

*no homogenous base paste
n.d. not determined
Base pastes represented by entries 1-7 were homogenous.

The invention claimed is:

1. A dental impression material comprising at least a polymerizable base paste (BP) and a non-aqueous catalyst paste (CP), wherein the base paste (BP) comprises about 0.001 to about 10% by weight of a water-stable anti-microbial agent and the catalyst component comprises a catalyst for polymerizing the base component and wherein the anti-microbial agent does not increase the time measured until the start of polymerization after combining components BP and CP by more than a factor of about 2, and wherein the anti-microbial agent is selected from the group consisting of salts of chlorhexidine (CHX), wherein CP is free of boric acid complexes, wherein the anti-microbial agent is the only anti-microbial agent present in the dental impression material.

2. The dental impression material according to claim 1, wherein the time measured until the start of polymerization after combining components BP and CP is influenced by the anti-microbial agent by a factor of about 0.5 to about 1.7.

3. The dental impression material according to claim 1, wherein the base paste (BP) comprises at least one compound comprising a polyether moiety or at least one compound comprising a siloxane moiety or both or at least one compound comprising a polyether moiety and a siloxane moiety.

4. The dental impression material according to claim 1, comprising at least one polymer selected from the group consisting of polyethers, polyesters, polyurethanes and polydimethylsiloxanes comprising at least two aziridino groups in the base paste.

5. The dental impression material according to claim 1, wherein the impression material is capable of curing via a ring-opening polymerization reaction of aziridines or via hydrosylation reaction.

6. The dental impression material according to claim 1, wherein the base paste (BP) comprises at least one polyaddition product or at least one polycondensation product having on average 2 aziridino groups or more and a molecular weight of at least about 500 or at least one organopolysiloxanes A1 with at least two ethylenically unsaturated groups per molecule.

7. The dental impression material according to claim 1, comprising a polyether having at least a proportion of tetrahydrofuran units.

8. The dental impression material according to claim 1, comprising
(A) at least one organopolysiloxanes A1 with at least two ethylenically unsaturated groups per molecule in the base or in the catalyst paste or in both,
(B) organohydrogenpolysiloxanes with at least 3 SiH groups per molecule in the base paste,
(C) optionally organopolysiloxanes without reactive groups in the base paste or in the catalyst paste or in both,
(D) a catalyst for promoting the reaction between A and B in the catalyst paste,
(E) optionally hydrophilizing agents in the base paste or in the catalyst paste or in both,
(F) fillers in the base paste or in the catalyst paste or in both,
(G) optionally conventional dental additives, adjuvants, plastizisers and colorants in the base paste or in the catalyst paste or in both,
(H) optionally at least one silane with at least two alkenyl groups per molecule and/or a polyether containing at least one unsaturated hydrocarbon in one molecule.

9. The dental impression material according to claim 8 comprising:
about 5-70 wt.-% components (A)+(B)+(H),
about 0-40 wt.-% component (C),
about 0.0005-0.05 wt.-% component (D), calculated as elemental platinum and related to the overall weight of the material present with the compounds (A) to (H),
about 0-10 wt.-% component (E),
about 10-90 wt.-% component (F),
about 0-5 wt.-% component (G),
about 0-50 wt.-% component (H), and
about 0.01 to 10% by weight of an anti-microbial agent.

10. A kit for producing dental impression materials, comprising at least one composition according to claim 1, with at least one polymerizable base paste BP and at least one non-aqueous catalyst paste CP, the components BP and CP being present separated from one another.

11. A device containing a dental impression material according to claim 1, wherein the device has the shape of a container, impression tray or a mixing device.

12. A method for disinfecting a dental impression material comprising the steps of:
providing a non-aqueous dental impression material as described in claim 1, which is set and germ contaminated; and
rinsing the set dental impression material with a non disinfecting liquid and leaving the impression material to dry or actively drying the impression material.

13. A method for the preparation of a dental impression material, wherein a base paste (BP) is prepared by mixing about 0.001 to about 10% by weight of a water-stable, anti-microbial agent with a polymerizable compound and a catalyst paste (CP) is prepared by mixing a catalyst for polymerizing the base component with one or more auxiliary compounds and wherein the anti-microbial agent does not increase the time measured until the start of polymerization after combining components BP and CP by more than a factor of about 2 and wherein the anti-microbial agent is selected from the group consisting of salts of chlorhexidine (CHX), wherein CP is free of boric acid complexes, wherein the anti-microbial agent is the only anti-microbial agent present in the dental impression material.

14. The dental impression material according to claim 1, wherein the base paste (BP) is substantially water-free.

15. The dental impression material according to claim 1, wherein salts of chlorhexidine (CHX) include at least one of chlorhexidine diacetate, chlorhexidine diacetate hydrate, chlorhexidine dihydrobromide, chlorhexidine dihydrochloride, chlorhexidine dinitrate, chlorhexidine sulphate, chlorhexidine carbonate, and a combination thereof.

16. The dental impression material according to claim 1, wherein the impression material is capable of curing via a ring-opening reaction of aziridines and wherein the salt of chlorhexidine is chlorhexidine diacetate hydrate.

17. The dental impression material according to claim 1, wherein the impression material is capable of curing via hydrosylation and wherein the salt of chlorhexidine is chlorhexidine diacetate hydrate.

* * * * *

UNITED STATES PATENT AND TRADEMARK OFFICE
CERTIFICATE OF CORRECTION

| | | |
|---|---|---|
| PATENT NO. | : 8,933,147 B2 | Page 1 of 3 |
| APPLICATION NO. | : 12/093869 | |
| DATED | : January 13, 2015 | |
| INVENTOR(S) | : Thomas Klettke et al. | |

It is certified that error appears in the above-identified patent and that said Letters Patent is hereby corrected as shown below:

Title page,
Column 2, item (57) (abstract), Line 5, Delete "ace." and insert -- according --, therefor.
Column 2, item (57) (abstract), Line 10, Delete "Hexitidin, Cetypyridininumcloride" and insert -- Hexetidine, Cetylpyridiniumchloride --, therefor.
Column 2, item (57) (abstract), Line 11, Delete "derivates" and insert -- derivatives --, therefor.

Page 2
Column 2 (other publications), Line 18, Delete "Indentification" and insert -- Identification --, therefor.

Page 3
Column 1 (other publications) Line 23, Delete "aI.," and insert -- al., --, therefor.
Column 1 (other publications) Line 31, Delete "aI.," and insert -- al., --, therefor.
Column 1 (other publications) Line 33, Delete "aI.," and insert -- al., --, therefor.
Column 1 (other publications) Line 50, Delete "aI.," and insert -- al., --, therefor.
Column 2 (other publications) Line 1, Delete "aI.," and insert -- al., --, therefor.
Column 2 (other publications) Line 4, Delete "aI.," and insert -- al., --, therefor.
Column 2 (other publications) Line 7, Delete "aI.," and insert -- al., --, therefor.
Column 2 (other publications) Line 10, Delete "aI.," and insert -- al., --, therefor.
Column 2 (other publications) Line 13, Delete "aI.," and insert -- al., --, therefor.
Column 2 (other publications) Line 15, Delete "aI.," and insert -- al., --, therefor.
Column 2 (other publications) Line 18, Delete "aI.," and insert -- al., --, therefor.
Column 2 (other publications) Line 21, Delete "aI.," and insert -- al., --, therefor.
Column 2 (other publications) Line 22-23, Delete "o/the Americal" and insert -- of the American --, therefor.
Column 2 (other publications) Line 31, Delete "aI.," and insert -- al., --, therefor.
Column 2 (other publications) Line 34, Delete "aI.," and insert -- al., --, therefor.
Column 2 (other publications) Line 36, Delete "aI.," and insert -- al., --, therefor.

Signed and Sealed this
Third Day of November, 2015

Michelle K. Lee
*Director of the United States Patent and Trademark Office*

Page 3
Column 2 (other publications) Line 37, Delete "o/the" and insert -- of the --, therefor.
Column 2 (other publications) Line 40, Delete "aI.," and insert -- al., --, therefor.
Column 2 (other publications) Line 47, Delete "aI.," and insert -- al., --, therefor.
Column 2 (other publications) Line 50, Delete "aI.," and insert -- al., --, therefor.

In the specification,
Column 3
Line 61, Delete "bactericins," and insert -- bacteriocins, --, therefor.
Line 62, Delete "parabenes," and insert -- parabens, --, therefor.

Column 4
Line 48, Delete "oxygene" and insert -- oxygen --, therefor.

Column 5
Line 26-27, Delete "bactericins," and insert -- bacteriocins, --, therefor.
Line 27-28, Delete "parabenes," and insert -- parabens, --, therefor.
Line 44, Delete "domiphene" and insert -- domiphen --, therefor.
Line 50, Delete "phtaldehyde" and insert -- pthaladehyde --, therefor.
Line 55-56, Delete "(glutaraldyde, phtaldehyde)" and insert -- (glutaraldehyde, pthaladehyde) --, therefor.
Line 56, Delete "chlorliexidine" and insert -- chlorhexidine --, therefor.
Line 65, Delete "diacatate" and insert -- diacetate --, therefor.

Column 6
Line 7, Delete "Mycobaterium." and insert -- Mycobacterium. --, therefor.

Column 7
Line 9, Delete "slilyl" and insert -- silyl --, therefor.
Line 11, Delete "slilyl" and insert -- silyl --, therefor.

Column 8
Line 22, Delete "tert.butyl," and insert -- tert-butyl, --, therefor.
Line 27, Delete "hereroaromatic" and insert -- heteroaromatic --, therefor.
Line 51, Before "be" delete "the".

Column 9
Line 1, Delete "polydipersity" and insert -- polydispersity --, therefor.

Column 10
Line 23, Delete "an" and insert -- on --, therefor.
Line 55, Delete "perfluoralkylated" and insert -- perfluoroalkylated --, therefor.

CERTIFICATE OF CORRECTION (continued)
U.S. Pat. No. 8,933,147 B2

Column 11
Line 22, Delete "silazides." and insert -- silanides. --, therefor.
Line 27, Delete "quarz," and insert -- quartz, --, therefor.

Column 12
Line 25, Delete "II" and insert -- II; --, therefor.
Line 46, Delete "penylene," and insert -- phenylene, --, therefor.

Column 13
Line 49, Delete "trimellithic" and insert -- trimellitic --, therefor.

Column 15
Line 59, Delete "lonol," and insert -- Ionol, --, therefor.

Column 16
Line 23, Delete "4OH" and insert -- 4 OH --, therefor.
Line 38, Delete "allylene" and insert -- alkylene --, therefor.
Line 54, Delete "epichlorohydrine" and insert -- epichlorohydrin --, therefor.

Column 20
Line 15, Delete "Borneo" and insert -- borneo --, therefor.
Line 15, Delete "illlipé" and insert -- illipé --, therefor.

Column 22
Line 17, Delete "text" and insert -- text. --, therefor.
Line 31, Delete "-5-" and insert -- -S- --, therefor.
Line 34, Delete "5-" and insert -- S- --, therefor.

Column 24
Line 34, Delete "microorganismsl" and insert -- microorganisms --, therefor.
Line 35, Delete "salviva." and insert -- salvia. --, therefor.
Line 54, Delete "setting" and insert -- setting. --, therefor.

Column 26
Line 19, Delete "(triscacylic" and insert -- (tricyclic --, therefor.
Line 26, Delete "tetafluoroborate" and insert -- tetrafluoroborate --, therefor.